(12) United States Patent
Kirsch et al.

(10) Patent No.: US 12,110,543 B2
(45) Date of Patent: Oct. 8, 2024

(54) SAMPLE TRANSFER TOOL

(71) Applicant: AXAGARIUS GMBH & CO. KG, Düren (DE)

(72) Inventors: Christoph Kirsch, Pulheim (DE); Elena Yaroshevskaya, Frechen (DE)

(73) Assignee: AXAGARIUS GMBH & CO. KG, Düren (DE)

( * ) Notice: Subject to any disclaimer, the term of this patent is extended or adjusted under 35 U.S.C. 154(b) by 807 days.

(21) Appl. No.: 16/791,799

(22) Filed: Feb. 14, 2020

(65) Prior Publication Data

US 2020/0263236 A1    Aug. 20, 2020

(30) Foreign Application Priority Data

Feb. 14, 2019   (DE) .......................... 102019201966.8

(51) Int. Cl.
| | |
|---|---|
| *C12Q 1/686* | (2018.01) |
| *A61K 31/715* | (2006.01) |
| *B01L 7/00* | (2006.01) |
| *C12Q 1/6806* | (2018.01) |
| *C12Q 1/6869* | (2018.01) |

(52) U.S. Cl.
CPC ............ *C12Q 1/686* (2013.01); *A61K 31/715* (2013.01); *B01L 7/52* (2013.01); *C12Q 1/6806* (2013.01); *C12Q 1/6869* (2013.01); *B01L 2300/0832* (2013.01)

(58) Field of Classification Search
CPC .... C12Q 1/686; C12Q 1/6806; C12Q 1/6869; B01L 7/52; B01L 2300/0832; B01L 3/02; B01L 3/021; A61K 31/715
See application file for complete search history.

(56) References Cited

U.S. PATENT DOCUMENTS

| | | | |
|---|---|---|---|
| 6,472,187 B1 | 10/2002 | Tonoike et al. | |
| 7,291,764 B1* | 11/2007 | Stice .................. | C12N 15/8778 800/24 |
| 10,934,540 B2 | 3/2021 | Hillebrand et al. | |
| 11,667,908 B2 | 6/2023 | Dommen et al. | |
| 2002/0012928 A1 | 1/2002 | Tonoike | |
| 2015/0037789 A1* | 2/2015 | Schiestl ............. | G01N 33/6893 435/7.1 |

FOREIGN PATENT DOCUMENTS

| | | |
|---|---|---|
| EP | 0 989 192 A2 | 3/2000 |
| EP | 1 069 190 A2 | 1/2001 |
| EP | 2 373 804 B1 | 11/2014 |
| WO | 2016/169679 A1 | 10/2016 |
| WO | 2017/027538 A1 | 2/2017 |

OTHER PUBLICATIONS

"Blutentnahmesysteme fur die Intensivmedizin" Erganzung zum Bluthassytem, 2011; English translation provided.
Grrunenwald, "Direct PCR from Whole Blood"; Epicentre, vol. 7, No. 4, 2004.

* cited by examiner

*Primary Examiner* — David C Thomas
(74) *Attorney, Agent, or Firm* — Norris McLaughlin, P.A.

(57) ABSTRACT

The invention relates to an active substance-coated rod-shaped sample transfer tool, the preparation thereof, and the use thereof for transferring nucleic acid-containing sample material into reaction mixtures of enzymatic detection reactions.

20 Claims, 24 Drawing Sheets
Specification includes a Sequence Listing.

Annealing temperature 55°C

Annealing temperature 52°C

SEQUENCE LISTING

```
<160> NUMBER OF SEQ ID NOS: 32

<210> SEQ ID NO 1
<211> LENGTH: 20
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 1
ggaatggcat tgacttggtc                                              20

<210> SEQ ID NO 2
<211> LENGTH: 19
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 2
gttctcggaa ccgatcaca                                               19

<210> SEQ ID NO 3
<211> LENGTH: 20
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 3
ctgaagcttt tggctttgag                                              20

<210> SEQ ID NO 4
```

```
<211> LENGTH: 19
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 4
ccgctgccaa attctttgg                                              19

<210> SEQ ID NO 5
<211> LENGTH: 18
<212> TYPE: DNA
<213> ORGANISM: Mus musculus

<400> SEQUENCE: 5
aacgacccct tcattgac                                               18

<210> SEQ ID NO 6
<211> LENGTH: 19
<212> TYPE: DNA
<213> ORGANISM: Mus musculus

<400> SEQUENCE: 6
tccacgacat actcagcac                                              19

<210> SEQ ID NO 7
<211> LENGTH: 15
<212> TYPE: DNA
<213> ORGANISM: Gallus gallus

<400> SEQUENCE: 7
ctcctacctc tacaa                                                  15

<210> SEQ ID NO 8
<211> LENGTH: 16
<212> TYPE: DNA
<213> ORGANISM: Gallus gallus

<400> SEQUENCE: 8
ggctagtgtt aggaat                                                 16

<210> SEQ ID NO 9
<211> LENGTH: 22
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 9
gagatgtttt tgctggtatt ga                                          22

<210> SEQ ID NO 10
<211> LENGTH: 23
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 10
aaygtataaa ccaatgcttc cat                                         23

<210> SEQ ID NO 11
```

```
<211> LENGTH: 19
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 11
gacgggaatt gaacccgcg                                                      19

<210> SEQ ID NO 12
<211> LENGTH: 22
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 12
gttatgcatg aacgtaatgc tc                                                  22

<210> SEQ ID NO 13
<211> LENGTH: 22
<212> TYPE: DNA
<213> ORGANISM: Glycine max

<400> SEQUENCE: 13
gccctctact ccaccccat cc                                                   22

<210> SEQ ID NO 14
<211> LENGTH: 23
<212> TYPE: DNA
<213> ORGANISM: Glycine max

<400> SEQUENCE: 14
gcccatctgc aagccttttt gtg                                                 23

<210> SEQ ID NO 15
<211> LENGTH: 25
<212> TYPE: DNA
<213> ORGANISM: Zea mays

<400> SEQUENCE: 15
ccgctgtatc acaagggctg gtacc                                               25

<210> SEQ ID NO 16
<211> LENGTH: 25
<212> TYPE: DNA
<213> ORGANISM: Zea mays

<400> SEQUENCE: 16
ggagcccgtg tagagcatga cgatc                                               25

<210> SEQ ID NO 17
<211> LENGTH: 23
<212> TYPE: DNA
<213> ORGANISM: Triticum aestivum

<400> SEQUENCE: 17
gtaacttcca aattcagaga aac                                                 23

<210> SEQ ID NO 18
<211> LENGTH: 24
<212> TYPE: DNA
<213> ORGANISM: Triticum aestivum
```

```
<400> SEQUENCE: 18
tctctaattt agaattagaa ggaa                                          24

<210> SEQ ID NO 19
<211> LENGTH: 21
<212> TYPE: DNA
<213> ORGANISM: Nicotiana tabacum

<400> SEQUENCE: 19
cacagtattt gctcgctgag a                                             21

<210> SEQ ID NO 20
<211> LENGTH: 19
<212> TYPE: DNA
<213> ORGANISM: Nicotiana tabacum

<400> SEQUENCE: 20
ccattgctgc ttcttctcc                                                19

<210> SEQ ID NO 21
<211> LENGTH: 24
<212> TYPE: DNA
<213> ORGANISM: Arabidopsis thaliana

<400> SEQUENCE: 21
ttaattcaaa aatcattttt cccg                                          24

<210> SEQ ID NO 22
<211> LENGTH: 22
<212> TYPE: DNA
<213> ORGANISM: Arabidopsis thaliana

<400> SEQUENCE: 22
tcaatgaaag tcccattctt tg                                            22

<210> SEQ ID NO 23
<211> LENGTH: 18
<212> TYPE: DNA
<213> ORGANISM: Vitis vinifera

<400> SEQUENCE: 23
ttccgaaccg aatcaagg                                                 18

<210> SEQ ID NO 24
<211> LENGTH: 17
<212> TYPE: DNA
<213> ORGANISM: Vitis vinifera

<400> SEQUENCE: 24
ggagcaccgt tccaagc                                                  17

<210> SEQ ID NO 25
<211> LENGTH: 19
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 25
cawcgatgaa gaacgyagc                                                19
```

```
<210> SEQ ID NO 26
<211> LENGTH: 20
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 26 rgtttcttt cctccgctta                                                 20

<210> SEQ ID NO 27
<211> LENGTH: 22
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 27
ggaagkaraa gtcgtaacaa gg                                             22

<210> SEQ ID NO 28
<211> LENGTH: 20
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 28 rgtttcttt cctccgctta                                                 20

<210> SEQ ID NO 29
<211> LENGTH: 22
<212> TYPE: DNA
<213> ORGANISM: Arteficial Sequence
<220> FEATURE:
<221> NAME/KEY: misc_feature
<223> OTHER INFORMATION: Primer

<400> SEQUENCE: 29
ccttatcayt tagaggaagg ag                                             22

<210> SEQ ID NO 30
<211> LENGTH: 20
<212> TYPE: DNA
<213> ORGANISM: Arteficial Sequence
<220> FEATURE:
<221> NAME/KEY: misc_feature
<223> OTHER INFORMATION: primer

<400> SEQUENCE: 30 rgtttcttt cctccgctta                                                 20

<210> SEQ ID NO 31
<211> LENGTH: 28
<212> TYPE: DNA
<213> ORGANISM: Capra hircus

<400> SEQUENCE: 31
ctagaggagc ctgttctata atcgataa                                       28

<210> SEQ ID NO 32
<211> LENGTH: 25
<212> TYPE: DNA
<213> ORGANISM: Capra hircus
```

```
<400> SEQUENCE: 32
tgacctaacg tctttatgtg tggtg                                    25
```

SAMPLE TRANSFER TOOL

PRIORITY CLAIM

This application claims priority of German Patent Application No. DE 10 2019 201 966.8, filed Feb. 14, 2019, the contents of which are hereby incorporated herein by reference.

FIELD OF THE INVENTION

The invention relates to an active substance-coated rod-shaped sample transfer tool, the preparation thereof, and the use thereof for transferring nucleic acid-containing sample material into reaction mixtures of enzymatic detection reactions.

BACKGROUND OF THE INVENTION

In direct PCR detection methods for whole blood and for plant material, two methods for sample preparation have become established to date:

A first method with simple sample preparation, such as dilution of the sample, or a quick lysis of the blood in a lysis buffer, in part combined with proteinase and/or incubation steps at elevated temperatures. For sample preparation, these methods typically require at least one reaction vessel, lysis buffer, optionally neutralization buffer and proteinase, incubation steps at elevated temperatures lasting 5 to 30 min, and pipette tips for transferring the solutions.

A second, "genuine" direct PCR method in which a blood aliquot is directly added to the PCR reaction as a template. For this, blood volumes of 0.2 to 5 µl are recommended for PCR mixtures of 10 to 50 µl.

The first method has the advantage that PCR inhibitors present in the blood can be destroyed or inactivated by the lysis, so that the following PCR can proceed more reliably, or the requirements on the robustness of the PCR reagents are lower. However, it has the disadvantage that more steps, materials and time is necessary as compared with the second method.

The second method has the advantage that the handling steps are extremely minimized, but has the disadvantage that the requirements on the robustness of the PCR system are substantially higher, since PCR inhibitors are carried into the PCR in fairly large amounts, because firstly the blood volume that arrives in the PCR is typically higher as compared to the first method, and because secondly inhibitors in the blood are by no means inactivated, retained or separated off before the start of the PCR. Thus, in the second method, an amount of sample is merely just introduced into the PCR without the sample having been subjected to any kind of treatment that exceeds beyond the transfer into the PCR.

Further, the second method has the disadvantage that, when typically 1 µl of blood is employed per 20 µl of PCR, the proteins of the blood will precipitate during the PCR, clearly color the PCR, and after the reaction or before the gel electrophoresis, a treatment is typically required, such as centrifugation of the sample or addition of proteinase for removal of turbidities, and thus preparation of the sample for DNA gel electrophoresis. Otherwise, the turbidities would impede or even prevent the gel-electrophoretic analysis of the PCR amplificates.

Further, in the second method, it is disadvantageous that, despite a high robustness of various PCR systems, the DNA amplification of some blood types (depending on the organism) nevertheless works insufficiently, and/or requires the addition of a very small amount of blood (clearly below 1 µl), especially if the PCR volume is limited to 10 µl, rather than performing 50 µl reactions, like in some methods of the prior art.

Experience shows that blood samples of less than 1 µl are difficult to handle, require specific pipette tips for the pipetting of submicroliter samples, and require more experience and attention of the user as compared to the pipetting of microliter samples.

Now, the object of the present invention has been to combine the advantages of the first method (inactivation of PCR inhibitors present in the blood) and of the second method (direct addition of blood into the PCR as a template), but without accepting the respective disadvantageous side effects. This should consider different body fluids including whole bloods, with different anticoagulants (EDTA, citrate, heparin), as well as different organisms (human, mouse, rat, rabbit, Guinea pig, chicken). Further, it is to be considered that the PCR is to be established in as small a volume as possible for cost reasons, but which is large enough to enable simple handling in an average laboratory, leading to acceptable results. Acceptable results are clearly recognizable amplificate bands in DNA gel electrophoresis. It has been found that a PCR volume of 10 µl is reasonable in this respect.

SUMMARY OF THE INVENTION

The idea underlying the invention is to incorporate some sample treatment into the procedure of sampling and transfer of the sample into the PCR, so that the sample transfer tool has an influence on the sample during the process of sample transfer, i.e., that the tool inactivates PCR inhibitors, for example, by binding PCR inhibitors or by releasing substances that inactivate PCR inhibitors, or at least reduces the adverse effect thereof, so that DNA amplification in the subsequent PCR can be improved, or made possible at all. It has been found that the transfer of very small amounts of blood as templates into a PCR including 10 µl can be performed very simply using a rod of suitable length, shape and material, coated with an active substance (e.g., anticoagulants). Thus, the present invention relates to (1) a rod-shaped or tubular sample transfer tool having at least one segment coated with one or more active substances, having an effect on a sample containing nucleic acids, so that materials contained in the sample that would inhibit an enzymatic reaction taking place after the transfer are bound at least in part, or inactivated;

(2) a process for preparing the rod-shaped or tubular sample transfer tool of aspect (1), comprising the treatment/coating of the starting sample transfer tool with one or more active substance(s);

(3) the use of the rod-shaped or tubular sample transfer tool of aspect (1) for the transfer of samples containing nucleic acids into an enzymatic reaction;

(4) a detection method, comprising:

(a) contacting the rod-shaped or tubular sample transfer tool of aspect (1) with a solid or liquid phase of a sample containing nucleic acids, so that a sufficient amount of said sample containing nucleic acids becomes adhered to said sample transfer tool;

(b) transferring the sample transfer tool to a reaction mixture for an enzymatic detection reaction, and immersing the sample transfer tool into the reaction mixture, so that an amount of said sample containing nucleic acids sufficient for the detection reaction is carried into the enzyme reaction;

(c) removing the sample transfer tool from the reaction mixture for said enzymatic detection reaction; und (d) performing said enzymatic detection reaction; and (5) a kit for performing the detection process of aspect (4), comprising one or more of the sample transfer tools of aspect (1).

DETAILED DESCRIPTION OF THE INVENTION

Figure 1:
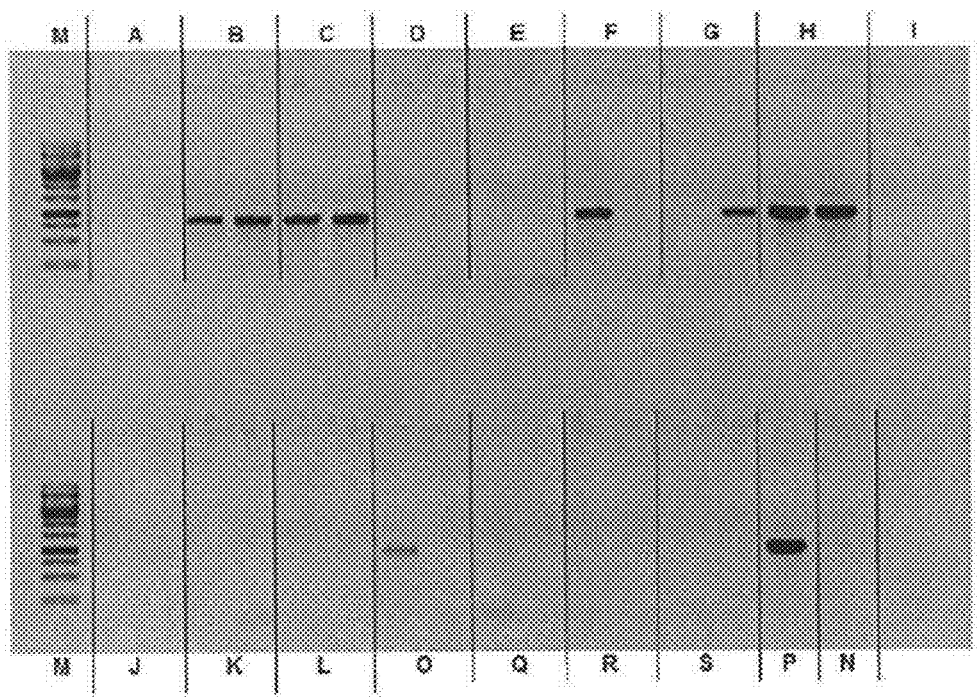
FIGS. 1-43 show the results of Examples 1-43.

The transfer of small sample amounts (e.g., blood or bacteria from a Petri dish) using a rod (e.g., a toothpick or pipette tip) has long been known and also applied ("Colony PCR"). The present invention is based on the surprising result that the sample transfer rod can be provided with an inhibitor-inactivating function by pretreating it with a suitable active substance. Those skilled in the art are sufficiently familiar with the fact that heparin as such has a strong PCR-inhibiting effect (cf. EP-B-2373804, page 2, paragraph 7), especially if purified DNA is used in PCR as a template. Those skilled in the art are also familiar with the fact that polyanions, such as heparin and other sulfated polysaccharides, can be employed as inhibitors of thermostable polymerases in PCR reactions (cf. U.S. Pat. No. 6,667,165). In EP-B-2373804, however, it has further been found that heparin-treated blood samples, and using such blood samples as templates in direct PCR, have less PCR-inhibiting effect as compared to blood samples anticoagulated with citrate or EDTA. Evidently, PCR-inhibiting effects of heparin and PCR inhibitors in the whole blood "neutralize" each other, so that heparinized blood functions substantially better as a template for PCR in direct PCR as compared to blood treated with EDTA or citrate. Surprisingly, it was found that rods (plastic toothpicks) treated with suitable active substances, such as heparin, can achieve the technical object. This led to the sample transfer tool according to the invention, the preparation thereof, and the use thereof according to aspects (1) to (5) as described above.

The sample transfer tool of aspect (1) of the invention preferably employs those active substances that inactivate materials from the sample material that inhibit an enzymatic detection reaction performed after the transfer. Further, it is preferred that the active substances are released into or dissolved in the sample upon contact with the sample.

Further, it is preferred that the active substances employed inactivate compounds that inhibit the enzymatic reaction performed after the transfer, or reduce their inhibiting effect. The sample transfer tool according to the invention can either bind said compounds/inhibitors by the active substances, or release the active substances to thereby inactivate the inhibitors. The sample transfer tool according to the invention is suitable for introducing sample material into an enzymatic reaction, especially a detection reaction. Said enzymatic detection reaction is preferably selected from PCR, reverse transcription, isothermal amplification, restriction digestion, sequencing and nucleic acid amplification, and the active substances are preferably selected from anticoagulants and polymeric compounds, such as heparin, chondroitin sulfate, heparan sulfate, keratan sulfate, amidopectins, hyaluronic acid, pectins, xanthan, chitosan, oligo-glucosamine, dextran sulfate, carrageenan, methylcellulose, guaran and other materials, such as chaotropic salts (e.g., barium, calcium and guanidinium perchlorates, -thiocyanates and -perchloroacetates), which are known to inactivate materials inhibiting enzymatic detection reactions. Said active substances are present on said sample transfer tool in a sufficient inhibitor-inhibiting amount, in which a coating of 0.001 bis 0.5, preferably 0.01 to 0.1 $IU/cm^2$ of sample transfer tool surface especially for heparin, a coating of 0.005 to 500, preferably from 0.02 to 25, $\mu g/cm^2$ of sample transfer surface, for other polysaccharides, and a coating of 0.1 to 50, preferably 1.5 to 4 $\mu mol/cm^2$ of sample transfer tool surface for chaotropic salts is present on said sample transfer tool.

The sample transfer tool according to the invention may have the shape of a rod, a pin, a needle, a tube or a pipette tip, and may be made of a solid material, such as plastic, wood, cardboard, paper, ceramics, glass, ceramics, clay, magnesia, metal, or combinations thereof. The sample transfer tool according to the invention may have a region designed for contact with the sample containing the nucleic acid, and which is coated with the active substances, and further have a region at which the sample transfer tool is held by the operator, including a human or a machine.

The sample transfer tool according to the invention should preferably be sized to be able to transfer a sample quantity of 10 to 500 nl, preferably 50 to 200 nl (or 10 to 500 μg, preferably 50 to 200 μg, in the case of solids). The sample transfer tool according to the invention should preferably be coated with said active substance(s) in such a way that a sufficient inhibitor-inhibiting amount of said active substance(s) is present in the sample transfer tool, e.g., amounts as defined above. In addition to the above mentioned active substances, the sample transfer tool according to the invention may also be coated with other neutral surfactants (such as polyoxyethylene derivatives of sorbitan monolaurate or sorbitan monopalmitate of the Tween® series, and polyoxyethylene derivatives of fatty alcohols of the Brij® series) and with salts (such as non-chaotropic salts and buffers).

Particularly preferred is a sample transfer tool consisting of a plastic rod, toothpick or plastic toothpick, and coated with heparin. For example, toothpicks, preferably plastic toothpicks of a specific kind, are suitable for this. After contacting the rod tip with the blood sample, about 50 to 200 nl of blood reliably adheres to the rod tip. If this tip is dipped into a 10 μl PCR mixture, the amount of blood is partially or wholly transferred into the PCR mixture. The amount of blood taken up and released by the rod can be controlled better or more exactly as compared to usual 0.5 to 10 μl pipette tips or wooden toothpicks. PCRs in a volume of 10 μl can be performed very well by this method with the following blood samples: human, cat, sheep, Guinea pig, cattle.

In the process according to the invention for preparing the sample transfer tool according to aspect (2) of the invention, the loading with active substances is effected either by immersing the starting sample transfer tool (the untreated rod or tube) once or several times into an aqueous solution comprising one or more active substances, followed by drying the sample transfer tool, or by covalently binding the active substance or substances to said starting sample transfer tool. The process that comprises immersing/drying is certainly preferred under commercial aspects. As already mentioned above, the active substances are preferably selected from anticoagulants and polymeric compounds, such as heparin, chondroitin sulfate, heparan sulfate, keratan sulfate, amidopectins, hyaluronic acid, pectins, xanthan, chitosan, oligo-glucosamine, dextran sulfate, carrageenan, methylcellulose, guaran and other materials known to inactivate materials inhibiting enzymatic reactions.

In the use according to aspect (3) of the invention, the enzymatic reaction is preferably an enzymatic detection reaction, which is selected, in particular, from PCR, reverse transcription, isothermal amplification, restriction digestion, sequencing and nucleic acid amplification. In this use, the following kinds of samples can be examined: body components and body fluids including blood, urine, saliva, cells, tissues and stool, plants and plant components including any kind of plant material, in which body fluids, plant material and stool specimens are particularly preferred.

In the detection method according to the invention of aspect (4), the sample transfer tool has an influence on the sample containing nucleic acids in such terms that substances contained in the sample that inhibit the enzymatic detection reaction are at least partially inactivated or bound. It is preferred that the enzymatic detection reaction is selected from PCR, reverse transcription, isothermal amplification, restriction digestion, sequencing and nucleic acid amplification. As set forth above for aspect (3), the samples may also be selected from body components and body fluids including blood, urine, saliva, cells, tissues and stool, plants and plant components including any kind of plant material, in which body fluids, plant material and stool specimens are particularly preferred. In both aspects (3) and (4), "transfer . . . into a reaction mixture" means that said reaction mixture may be in an open or closable reaction vessel, in a well of a (micro)titration plate, or on a planar plate.

In the detection method according to the invention, steps (a) and (b) can be performed independently of one another, manually by an operator, or by a machine. It is preferred for steps (a) and (b) to transfer a sample quantity of 10 to 500 nl, preferably 50 to 200 nl (or 10 to 500 µg, preferably 50 to 200 µg, in the case of solids). Further, it is preferred for the reaction volume of the detection reaction to be 1 to 100 µl, preferably about 10 µl. Optionally, lysis of the sample material may be performed in the detection method according to the invention before said contacting of step (a).

The kit according to aspect (5) of the invention may further include reagents, reaction mixtures and/or solvents for the detection reaction and/or reagents for the lysis of the sample material.

The invention is explained in more detail using the following Examples. However, these do not in any way limit the claimed subject matter.

EXAMPLES

Materials and Methods

Generally for all experiments unless stated otherwise:

Preparation of Sample Transfer Tool:

A rod, for example, a commercially available plastic toothpick, is immersed, for some seconds to some minutes, into a solution consisting of an aqueous solution containing: as an active substance: 38 IU heparin per ml or another active substance as stated in the Examples; as an auxiliary agent: 10% Polysorbate 20 (CAS No. 9005-64-5, trade name, e.g., Tween®20) or poly(propylene glycol) (CAS 25322-69-4, average molecular weight: 2700 g/mol). After drying for at least one hour, the tool is used for sample transfer.

PCR Mix:

MACHEREY-NAGEL NucleoType HotStart PCR Master Mix containing Hotstart Taq DNA polymerase, buffer, magnesium ions, dNTPs, red stain. A reaction mixture of 10 µl contains: 5 µl NucleoType HotStart PCR Master Mix, 0.2 µM of each primer, water. Into this reaction mixture, the sample is added by means of the transfer tool. Typical reaction mixture for the PCR for one sample: 5 µl NucleoType HotStart PCR Master Mix; 0.2 µl Primer A (10 µM); 0.2 µl Primer B (10 µM); 4.6 µl water; 10 µl total volume.

Sample Transfer:

The tool is briefly (for about one second) pricked into the sample by about 1-5 mm deep, and thereafter briefly (for about one second) dipped into the PCR without performing any other mixing or stirring movements.

PCR Device:

As the PCR device, either a MasterCycler Gradient (Eppendorf company) or a Thermocycler GeneExplorer Triple or Thermocycler GeneExplorer Advanced (JoJo Life Sciences company) was used.

Analysis of PCR Products:

After performing the PCR, the reaction mixtures were analyzed by gel electrophoresis (1% agarose gel in TAE buffer, staining with ethidium bromide) or using an Agilent 2100 Bioanalyzer and Agilent DNA 1000 Kit in accordance with the manufacturer's instructions.

TABLE 1

Primers employed

| Primer pair # | SEQ ID NO: | Sequence 5' - 3' | Size of amplificate (bp) | Target region Mt: mitochondrial Nc: nucleus-coded aSp: across species Spsp: species-specific |
|---|---|---|---|---|
| 1 | 1 | F: GGAATGGCATTGACTTGGIC | 813 | Bitter-Taste Receptor Gene Repertoire in Different Lagomorphs Species |
|   | 2 | R: GTTCTCGGAACCGATCACA |   |   |
| 2 | 3 | F: CTGAAGCTTTTGGCTTTGAG | female: 331 bp male: 302 + 331 bp | Nc, sex determination |
|   | 4 | R: CCGCTGCCAAATTCTTTGG |   |   |
| 3 | 5 | F: AACGACCCCTTCATTGAC | 191 | Nc, GAPDH, aSp, in mouse genome: several tens up to about 200 targets |
|   | 6 | R: TCCACGACATACTCAGCAC |   |   |

TABLE 1-continued

Primers employed

| Primer pair # | SEQ ID NO: | Sequence 5' - 3' | Size of amplificate (bp) | Target region<br>Mt: mitochondrial<br>Nc: nucleus-coded<br>aSp: across species<br>Spsp: species-specific |
|---|---|---|---|---|
| 14 | 7 | F: CTCCTACCTCTACAA | 415 | Spsp, chicken |
|  | 8 | R: GGCTAGTGTTAGGAAT |  |  |
| 5 | 9 | F: GAGATGTTTTTGCTGGTATTGA | 308 | ManyPlants |
|  | 10 | R: AAYGTATAAACCAATGCTTCCAT |  |  |
| 6 | 11 | F: GACGGGAATTGAACCCGCG | 447 | ManyPlants |
|  | 12 | R: GTTATGCATGAACGTAATGCTC |  |  |
| 7 | 13 | F: GCCCTCTACTCCACCCCCATCC | 118 | Spsp, soybean |
|  | 14 | R: GCCCATCTGCAAGCCTTTTTGTG |  |  |
| 8 | 15 | F: CCGCTGTATCACAAGGGCTGGTACC | 226 | Spsp, maize |
|  | 16 | R: GGAGCCCGTGTAGAGCATGACGATC |  |  |
| 9 | 17 | F: GTAACTTCCAAATTCAGAGAAAC | 201 | Spsp, wheat |
|  | 18 | R: TCTCTAATTTAGAATTAGAAGGAA |  |  |
| 10 | 19 | F: CACAGTATTTGCTCGCTGAGA | 422 | Spsp, tobacco |
|  | 20 | R: CCATTGCTGCTTCTTCTCC |  |  |
| 11 | 21 | F: TTAATTCAAAAATCATTTTTCCCG | 230 | Spsp, *Arabidopsis* |
|  | 22 | R: TCAATGAAAGTCCCATTCTTTG |  |  |
| 12 | 23 | F: TTCCGAACCGAATCAAGG | 193 | *Vitis vinifera* |
|  | 24 | R: GGAGCACCGTTCCAAGC |  |  |
| 13 | 25 | F: CAWCGATGAAGAACGYAGC | 418 | ASp, plants, fungi |
|  | 26 | R: RGTTTCTTTTCCTCCGCTTA |  |  |
| 14 | 27 | F: GGAAGKARAAGTCGTAACAAGG | 745 | ASp, plants, fungi |
|  | 28 | R: RGTTTCTTTTCCTCCGCTTA |  |  |
| duplex 15 (13) | 29 | F: CCTTATCAYTTAGAGGAAGGAG | 757 | ASp, plants, fungi |
|  | 30 | R: RGTTTCTTTTCCTCCGCTTA |  |  |
|  | 25 | F: CAWCGATGAAGAACGYAGC | 418 |  |
|  | 26 | R: RGTTTCTTTTCCTCCGCTTA |  |  |
| 16 | 31 | F: CTAGAGGAGCCTGTTCTATAATCGATAA | 142 | Spsp, goat |
|  | 32 | R: TGACCTAACGTCTTTATGTGTGGTG |  |  |

TABLE 2

PCR programs and devices employed

| PCR program # | Program | Device |
|---|---|---|
| 1 | 1x: 95° C. 2 min<br>40x: 95° C., 15 s; 55° C., 15 s; 72° C., 15 s<br>1x: 72° C., 1 min cooling | Eppendorf Gradient Cycler |
| 2 | 1x: 95° C. 2 min<br>40x: 95° C., 15 s; 60° C., 15 s; 72° C., 15 s<br>1x: 72° C., 1 min cooling | Eppendorf Gradient Cycler |
| 3 | 1x: 95° C. 2 min<br>40x: 95° C., 15 s; 38° C., 15 s; 72° C., 15 s<br>1x: 72° C., 1 min cooling | Eppendorf Gradient Cycler |
| 4 | 1x: 95° C. 2 min<br>40x: 95° C., 15 s; 65° C., 15 s; 72° C., 15 s<br>1x: 72° C., 1 min cooling | Eppendorf Gradient Cycler |
| 5 | 1x: 95° C. 2 min<br>40x: 95° C., 15 s; 52° C., 15 s; 72° C., 15 s<br>1x: 72° C., 1 min cooling | Eppendorf Gradient Cycler |
| 6 | 1x: 95° C. 2 min<br>40x: 95° C., 15 s; 60° C., 20 s; 72° C., 30 s<br>1x: 72° C., 1 min cooling | Thermocycler GeneExplorer Advanced |
| 7 | 1x: 95° C. 2 min<br>40x: 95° C., 15 s; 55° C., 30 s; 72° C., 1 min<br>1x: 72° C., 1 min cooling | Thermocycler GeneExplorer Advanced |
| 8 | 1x: 95° C. 2 min<br>40x: 95° C., 15 s; 60° C., 30 s; 72° C., 1 min<br>1x: 72° C., 1 min cooling | Thermocycler GeneExplorer Advanced |
| 9 | 1x: 95° C. 2 min<br>40x: 95° C., 15 s; 55° C., 20 s; 72° C., 30 s<br>1x: 72° C., 1 min cooling | Thermocycler GeneExplorer Advanced |
| 10 | 1x: 95° C. 2 min<br>40x: 95° C., 15 s; 65° C., 20 s; 72° C., 30 s<br>1x: 72° C., 1 min cooling | Thermocycler GeneExplorer Advanced |
| 11 | 1x: 95° C. 2 min<br>40x: 95° C., 15 s; 52° C., 30 s; 72° C., 1 min<br>1x: 72° C., 1 min cooling | Thermocycler GeneExplorer Advanced |

TABLE 2-continued

PCR programs and devices employed

| PCR program # | Program | Device |
|---|---|---|
| 12 | 1x: 95° C. 2 min<br>40x: 95° C., 15 s; 55° C., 20 s; 72° C., 30 s<br>1x: 72° C., 1 min cooling | GET3X Thermal Cycler |
| 13 | 1x: 98° C. 5 min<br>40x: 98° C., 5 s; 55° C., 5 s; 72° C., 20 s<br>1x: 72° C., 1 min cooling | Eppendorf Gradient Cycler |
| 14 | 1x: 94° C. 3 min<br>30x: 94° C., 30 s; 55° C., 30 s; 72° C., 20 s<br>1x: 72° C., 10 min cooling | Eppendorf Gradient Cycler |
| 15 | 1x: 95° C. 3 min<br>30x: 95° C., 15 s; 55° C., 15 s; 72° C., 45 s<br>cooling | Eppendorf Gradient Cycler |
| 16 | 1x: 95° C. 3 min<br>35x: 95° C., 20 s; 55° C., 30 s; 72° C., 30 s<br>1x: 72° C., 1 min cooling | Eppendorf Gradient Cycler |
| 17 | 1x: 95° C. 2 min<br>40x: 95° C., 15 s; 60° C., 20 s; 72° C., 30 s<br>1x: 72° C., 1 min cooling | GET3X Thermal Cycler |
| 18 | 1x: 95° C. 2 min<br>40x: 95° C., 15 s; 60° C., 30 s; 72° C., 30 s<br>1x: 72° C., 1 min cooling | GET3X Thermal Cycler |

Overview

Examples Group I: Blood samples (heparin-treated sample transfer tools).

Example 1: Different heparin concentrations in water and Tween® 20

Example 2: Different immersion depths

Example 3: Tween® 10% and Brij 1% as auxiliary agents

Example 4: 20 replicates. Control: Tween® without heparin

Example 5: 20 replicates. Control: Untreated sample transfer tool

Example 6: Immersion depths in heparin and blood

Example 7: Robustness of tool: mechanical action and other

Example 8: Various blood samples

Examples group II: Plant leaf specimens (heparin-treated sample transfer tools)

Example 9: Wheat, maize, cotton: tool treated vs. untreated

Example 10: Soybean: tool treated vs. untreated

Example 11: Soybean, wheat, maize, tobacco: tool treated. Simple controls

Example 12: Arabidopsis, sampling: piercing, scratching

Example 13: Tobacco, sampling: pricking, scratching. Duration of sample transfer: 0-4 s Example 14: Tobacco, sampling and transfer: pricking, scratching, 1×, 2× dipping, stirring in Example 15: Mechanical stability of the coating. Tobacco Example 16: Duplex PCR tobacco-grape vine, Bioanalyzer Example 17: Soybean, cotton, wheat, amplicon 418 bp Example 18: Cotton, wheat, amplicon 745 bp Example 19: Tobacco, vine leaves: after sampling, direct sample transfer vs. drying of sample Example 20: Duplex PCR soybean, cotton, wheat, 418 bp+757 bp Example 21: Sampling: pricking vs. piercing, tobacco, grape vine Example 22: Coating procedure: individually or in bunches Example 23: Comparison: Lysate vs. direct sample transfer. Tobacco, cotton Example 24: PCR volume 10-50 µl, tobacco, cotton Example 25: Storage of coating: fresh vs. 2 months at −20° C. to +37° C.

Example 26: Comparison of products

Examples group III: Other kinds of samples

Example 27: avocado flesh: tool+/−heparin

Example 28: avocado flesh: tool+/−heparin

Examples group IV: Different active substances

Example 29: Chondroitin sulfate 5%, 1% as compared to heparin and negative control Example 30: Dextran sulfate 0.1-5% as compared to heparin control and NK, mouse EDTA blood Example 31: Solution of chaotropic salt instead of heparin Example 32: Carrageenan 0.05-0.5%, rabbit blood Example 33: Dextran sulfate 0.01%-1.5% with tobacco Example 34: Arabidopsis: heparin, dextran vs. uncoated and NK Example 35: Maize: dextran 0.001%, 0.005%, 0.01% vs. uncoated Example 36: GITC and GuHCl+/−Tween® with vine leaf Example 37: Tween® as auxiliary agent replaced by water or propylene glycol with leaves and blood Example 38: λ-Carrageenan with blood Example 39: λ-Carrageenan with meat (goat)

Examples group V: Different materials and shapes of the sample transfer tool

Example 40: Toothpick, pipette tips, paper clip

Example 41: Combitips interior part, paper clip with cotton leaf

Example 42: Polystyrene rods from weighing boats with blood

Example 43: Pipette tip with blood

Example 1: Different Heparin Concentrations in Water and Tween®20

Sample material: EDTA-treated rabbit blood

Description of tool (kind and amount of active substances and auxiliary agents): Plastic toothpick coated with Li-heparin+/−Tween® 20 at different amounts.

Coating solutions:

Heparin amount in International Units (IU) per 500 µl

Water: 120 IU; 12 IU OW (from previous day); 1.2 IU fr. (freshly prepared); 0.12 IU.

0.1% Tween® 20: 120 IU; 12 IU; 1.2 IU; 0.12 IU, 0 IU.

P: Positive control: 50 µl blood treated with 1.5 IU of heparin, toothpick untreated N: Blood untreated, sample transfer tool untreated Primer: Primer pair #1

PCR program: #2

The result is shown in FIG. 1 (heparin quantity in international units (IU) per 500 µl): M—marker; A—120 IU heparin in water; B—12 IU heparin in water, from previous day; C—12 IU heparin in water, freshly prepared; D—1.2 IU heparin in water; E—0.12 IU heparin in water; F—0 IU heparin in water; G—120 IU heparin in 0.1% Tween® 20; H—12 IU heparin in 0.1% Tween®20; I—1.2 IU heparin in 0.1% Tween® 20; J—0.12 IU heparin in 0.1% Tween® 20; K—0 IU heparin in 0.1% Tween® 20; L—120 IU heparin in 1% sucrose; 0-12 IU heparin in 1% sucrose; Q—1.2 IU heparin in 1% sucrose; R—0.12 IU heparin in 1% sucrose; S—0 IU heparin in 1% sucrose; P—positive control: 50 µl blood treated with 1.5 IU heparin, toothpick untreated; N—Blood untreated, toothpick untreated Conclusion:

When a sample transfer tool coated with a solution of heparin in a suitable concentration in water or in 0.1% Tween® 20 is used, an amplificate forms in PCR, whereas when an untreated toothpick is used for sample transfer, no amplification occurs (N). In the positive control (P), the blood was treated with heparin before it was transferred with an untreated toothpick into the PCR.

Example 2; Different Immersion Depths

Figure 2:
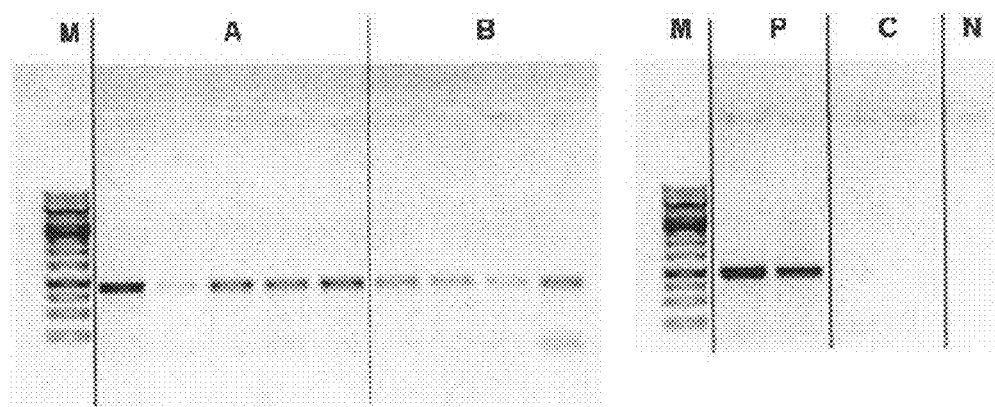

Sample material: EDTA-treated rabbit blood
Description of tool (kind and amount of active substances and auxiliary agents): Plastic toothpick coated with Li-heparin/Tween® 20. Toothpick immersed to different depths into solution for coating.
Coating solutions:
120 IU heparin in 500 µl 0.1% Tween®, toothpick immersed to 10 mm or 2 mm into coating solution, P: positive control: 50 µl blood treated with 1.5 IU heparin, toothpick untreated, without heparin: rod uncoated, N: PCR without sample addition
Primer: Primer pair #1
PCR program: #2
The result is shown in FIG. 2: M—marker; A—120 IU heparin in 500 µl 0.1% Tween®, toothpick immersed to 10 mm into coating solution; B—120 IU heparin in 500 µl 0.1% Tween®, toothpick immersed to 2 mm into coating solution; C—without heparin: toothpick uncoated; P—positive control: 50 µl blood treated with 1.5 IU heparin, toothpick untreated; N—negative control: PCR without template addition Conclusion:

When a sample transfer tool immersed to 2 mm or 10 mm deep into the coating solution for coating was used, PCR amplificates are obtained, whereas when the sample is transferred using an uncoated toothpick, no PCR amplificates are formed.

Example 3: Tween® 10% and Brij 1% as Auxiliary Agents

Figure 3:
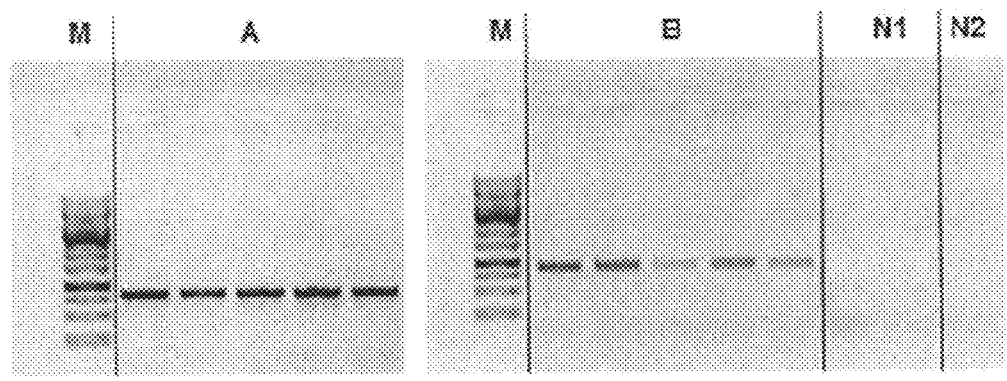

Sample material: EDTA-treated rabbit blood
Description of tool (kind and amount of active substances and auxiliary agents): Plastic toothpick coated with the following solutions: 20 IU heparin in 500 µl solution 10% Tween® 20 or 1% Brij® 58 (CAS 9004-95-9)
Negative control "without heparin"=toothpick untreated
N: negative control, PCR without template
Primer: Primer pair #1
PCR program: #2
The result is shown in FIG. 3: M—marker; A—20 IU heparin in 500 µl solution 10% Tween®20; B—20 IU heparin in 500 µl solution 1% Brij® 58; N1—Negative control "without heparin", toothpick untreated; N2—negative control, PCR without template Conclusion:

When a toothpick coated with heparin dissolved in 10% Tween®20 or in 1% Brij® 58 is used, PCR amplificates are formed, whereas sample transfer with an uncoated toothpick does not form amplificates. Thus, not only the surfactant Tween®20, but also the surfactant Brij®58 can be used as an auxiliary agent.

Example 4: 20 Replicates. Control: Tween without Heparin

Figure 4:
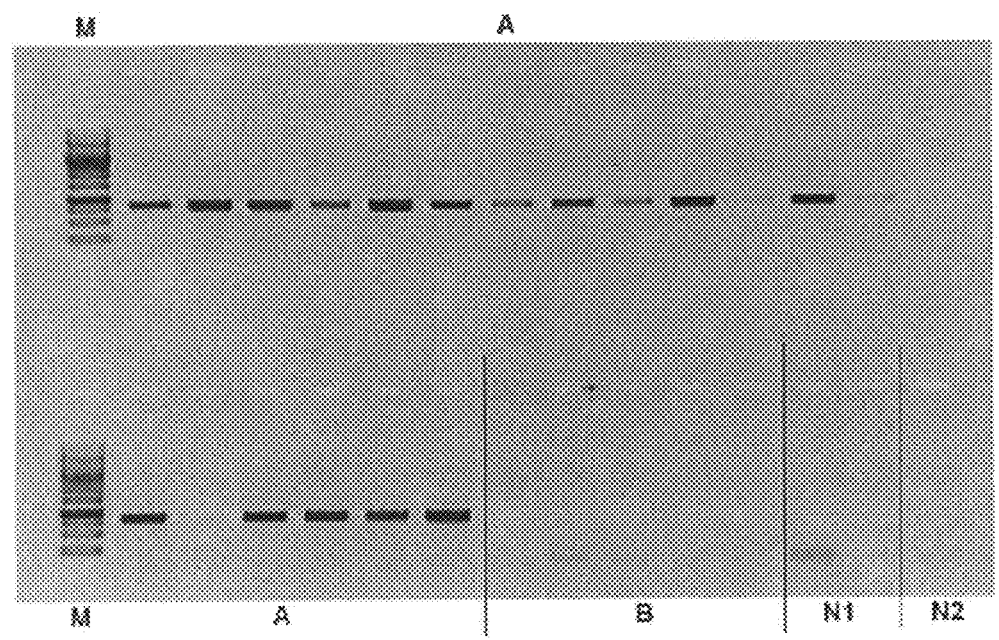

Sample material: EDTA-treated rabbit blood
Description of tool (kind and amount of active substances and auxiliary agents): Plastic toothpick coated with A: 20 IU heparin/500 µl 10% Tween®20 (20 replicates); B: 10% Tween®20 (5 replicates);
Sample transfer: For sample uptake, the toothpicks were immersed in 3 µl blood aliquots.
Primer: Primer pair #1
PCR program: #2
The result is shown in FIG. 4: M—marker; A—20 IU heparin/500 µl 10% Tween®20 (20 replicates); B—10% Tween®20 without heparin (5 replicates); N1—negative control: untreated toothpicks; N2—negative control: PCR without template addition Conclusion:

When toothpicks coated only with Tween20 solution are used for sample transfer, 5 out of 5 reactions do not yield any amplificates, whereas when toothpicks coated with heparin/Tween® solution are used, 19 out of 20 reactions form amplificates. Thus, Tween®20 is an auxiliary agent (surfactant, wetting agent) rather than an active substance.

Example 5: 20 Replicates. Control: Untreated Sample Transfer Tool

Figure 5:
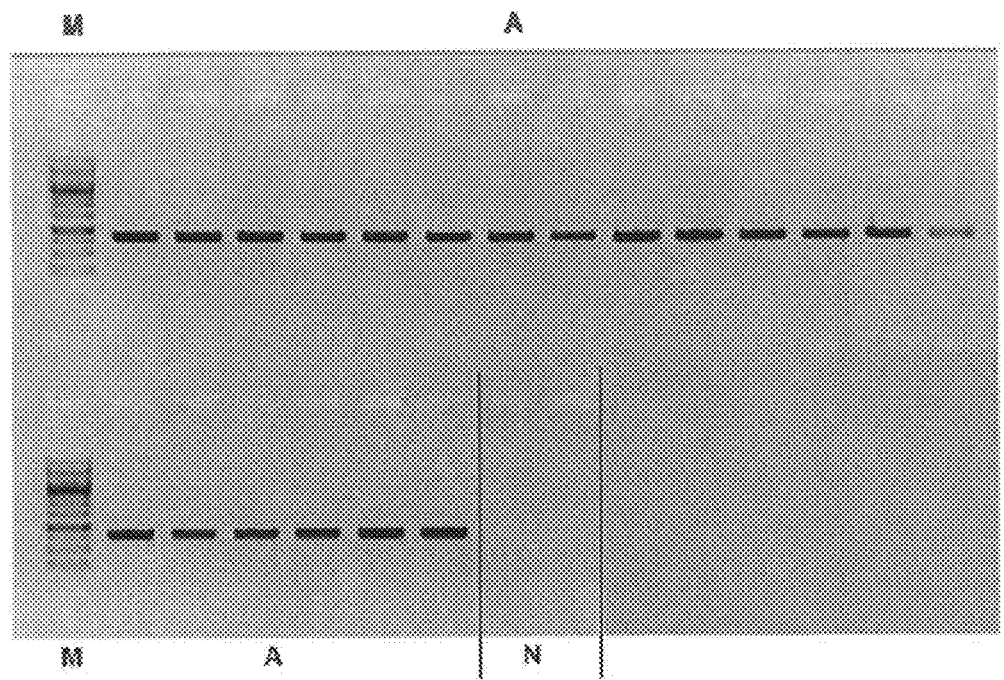

Sample material: EDTA-treated rabbit blood
Description of tool (kind and amount of active substances and auxiliary agents): 20 IU heparin/500 µl 10% Tween®20 (20 replicates)
Sample transfer: For sample uptake, the toothpicks were immersed into 10 µL blood aliquots
Primer: Primer pair #1
PCR program: #2
The result is shown in FIG. 5: M—marker; A—20 IU heparin/500 µl 10% Tween®20 (20 replicates); N—negative control: Untreated toothpicks Conclusion:

When toothpicks coated with heparin/Tween® solution are used for sample transfer and immersed deep into 10 µl blood aliquots for sample uptake, 20 of 20 reactions yield amplificates, whereas when untreated toothpicks are used, 2 of 2 reactions do not form amplificates.

Example 6: Immersion Depths in Heparin and Blood

Figure 6:
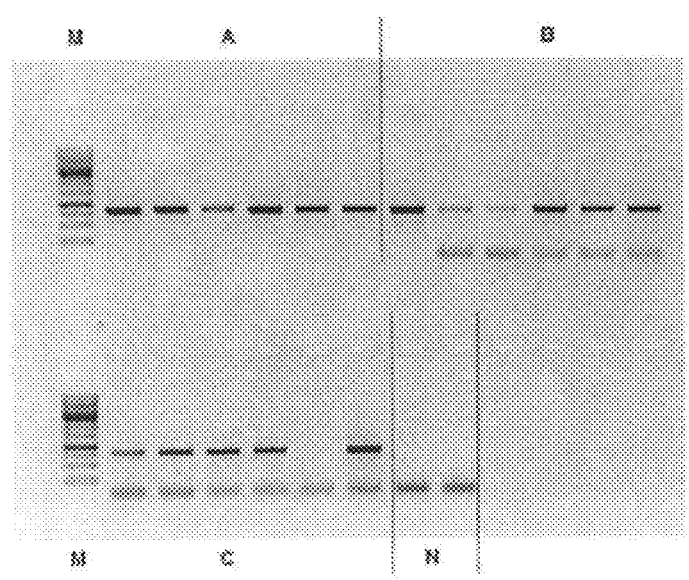

Sample material: EDTA-treated rabbit blood
Description of tool (kind and amount of active substances and auxiliary agents): Plastic toothpick. Coating solution: 38 IU heparin/ml solution containing 10% Tween®20. Different immersion depths of the toothpicks into the coating solution: 9 mm, 5 mm, 13 mm. Different immersion depths of the coated toothpicks into the blood: 5 mm, 13 mm. Immersion depths of the blood-loaded toothpick into the PCR: about 3 mm for all.
Primer: Primer pair #1
PCR program: #2
The result is shown in FIG. 6: Immersion depths of the toothpick; M: marker, DNA ladder; A: Heparin solution 10 mm, blood 5 mm; B: Heparin solution 5 mm, blood 13 mm; C: Heparin solution 13 mm, blood 13 mm; N: Untreated toothpicks, blood 5 mm Conclusion:

When toothpicks treated with heparin solution are used for sample transfer of blood into the PCR, amplificates can be formed with different immersion depths of the toothpicks into the heparin solution for coating as well as with different immersion depths into the PCR for releasing the blood, whereas no amplificates are formed when the blood is transferred with uncoated toothpicks.

Example 7: Robustness of Tool: Mechanical Action and Other

Sample material: EDTA-treated rabbit blood

Description of tool (kind and amount of active substances and auxiliary agents): Plastic toothpick, coating solution: 38 IU heparin/ml solution containing 10% Tween20.

Primer: Primer pair #1

PCR program: #2

Figure 7:
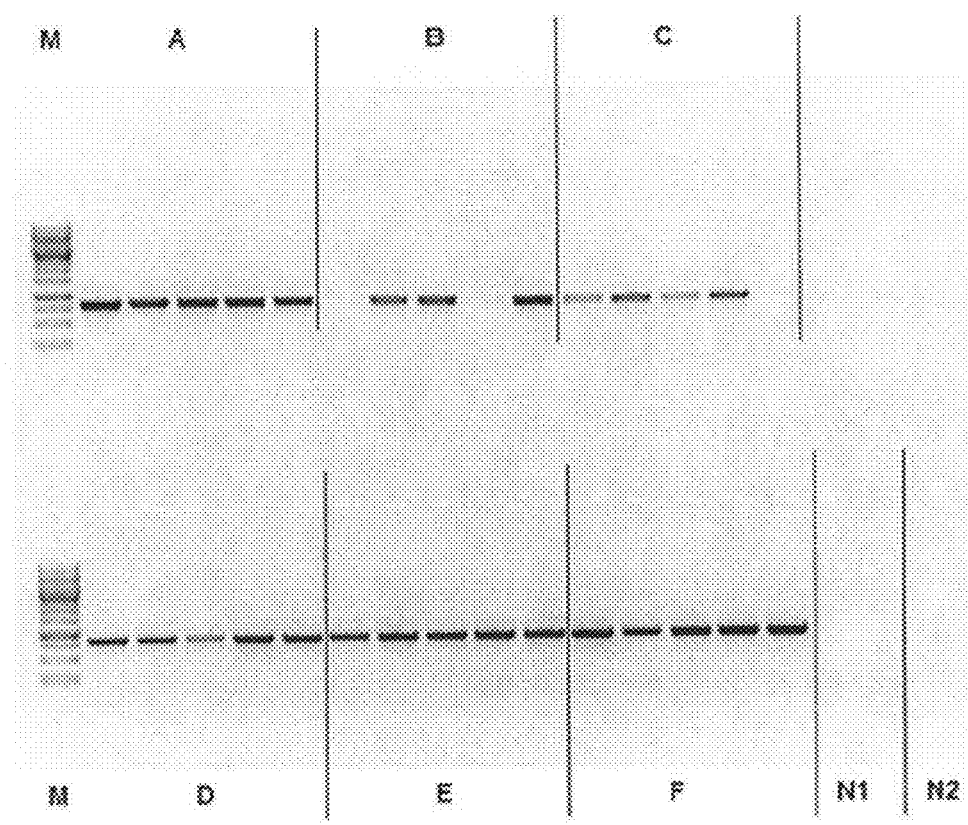

The result is shown in FIG. 7: A: Freshly prepared sample transfer tools, contact of the blood-loaded tool with the PCR for one second; B: the same, but contact of the blood-loaded tool with the PCR for five seconds; C: the same, but contact of the blood-loaded tool with the PCR with tumbling movement in the PCR for about three seconds; D: like A), but drop sample transfer tool on the table before the blood uptake/use in order to test the mechanical stability of the coating; E: like A), but using sample transfer tools that were about five weeks old; F: like D), but using sample transfer tools that were about five weeks old; N1: using untreated tools for blood transfer; N2: PCR negative control (no template control)

Conclusion:

Toothpicks coated with heparin are stable on storage for at least several weeks, withstand mechanical stress (dropping). The introducing of the blood sample into the PCR can be effected by a short contact (about one second), but also, albeit with slightly lower success, by longer contact of stirring in.

Example 8: Various Blood Samples

Sample material: EDTA-treated rabbit blood, EDTA-treated mouse blood, citrate-treated mouse blood, EDTA-treated rat blood, EDTA-treated chicken blood Description of tool (kind and amount of active substances and auxiliary agents): Plastic toothpick, 38 IU heparin/ml of 10% Tween®20 solution Primer: Primer pair #1 (rabbit), primer pair #2 (mouse), primer pair #3 (rat), primer pair #4 (chicken)

PCR program: #2 for rabbit, mouse, rat, and #3 for chicken

Figure 8:
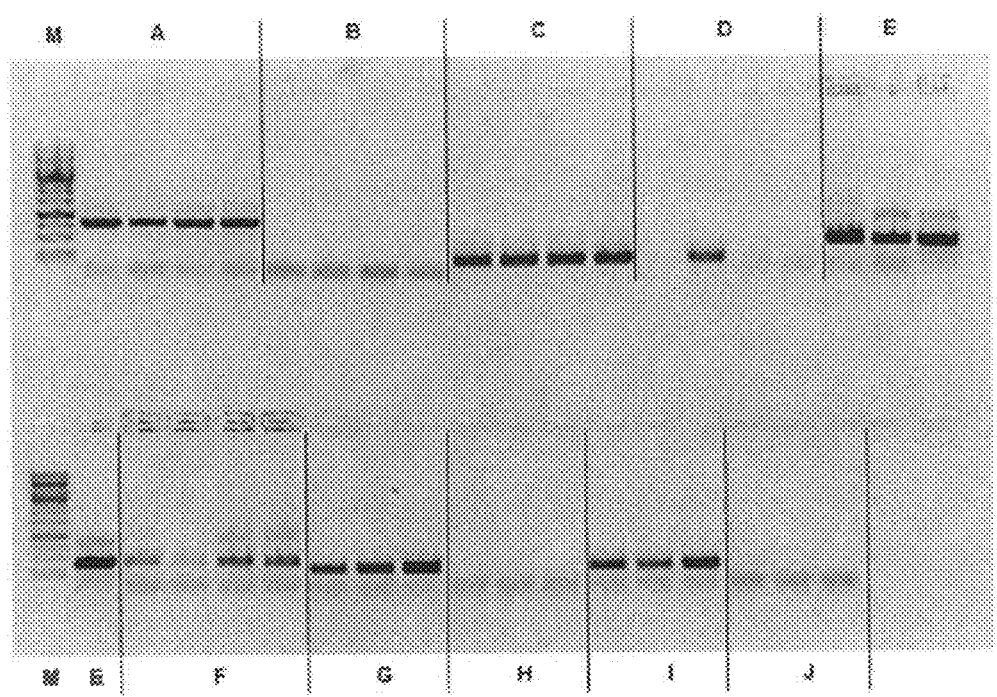

The result is shown in FIG. 8: M: marker—DNA ladder; A: EDTA-treated rabbit blood, heparin-coated toothpick; B: EDTA-treated rabbit blood, uncoated toothpick; C: EDTA-treated rat blood, heparin-coated toothpick; D: EDTA-treated rat blood, uncoated toothpick; E: EDTA-treated chicken blood, heparin-coated toothpick; F: EDTA-treated chicken blood, uncoated toothpick; G: EDTA-treated mouse blood, heparin-coated toothpick; H: EDTA-treated mouse blood, uncoated toothpick; I: citrate-treated mouse blood, heparin-coated toothpick; J: citrate-treated mouse blood, uncoated toothpick Conclusion:

The use of toothpicks for the transfer of blood sample aliquots into the PCR enables or improves the formation of amplificates in PCR if they are coated with heparin as compared to uncoated toothpicks. This holds for blood samples from different organisms and anticoagulants.

Examples Group II: Plant Leaf Specimens

Example 9: Wheat, Maize, Cotton; Tool Treated Vs. Untreated

Sample material: Leaf material from wheat, maize, cotton

Description of tool (kind and amount of active substances and auxiliary agents): Plastic toothpick treated with 38 IU heparin/ml of 10% Tween®20 solution.

Primer: Primer pair #5 (cotton), primer pair #6 (wheat and maize)

PCR program: #1

Figure 9:
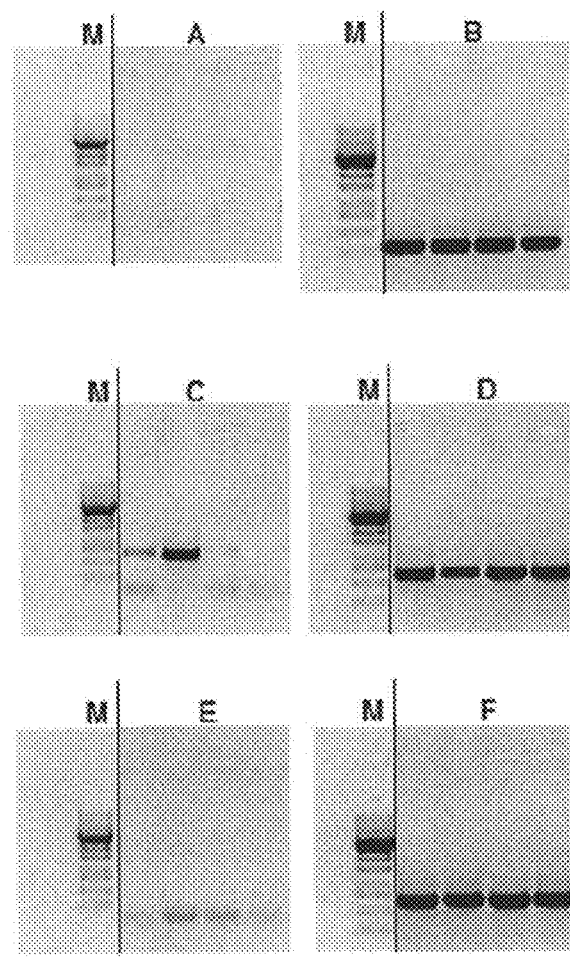

The result is shown in FIG. 9: M—marker; A—cotton, untreated tool; B—cotton, heparin-treated tool; C—wheat, untreated tool; D—wheat, heparin-treated tool; E—maize, untreated tool; F—maize, heparin-treated tool Conclusion:

The use of heparin-coated toothpicks for the transfer of sample material from wheat, maize and cotton leaves results in the formation of expected amplification products. For wheat and maize, an 447 bp amplificate was formed, and for cotton, a 308 bp amplificate was formed.

Example 10: Soybean: Tool Treated Vs. Untreated

Sample material: Plant leaf material from soybean

Description of tool (kind and amount of active substances and auxiliary agents): 40 IU heparin/ml of 10% Tween®20

Primer: Primer pair #6

PCR program: #2

Figure 10:
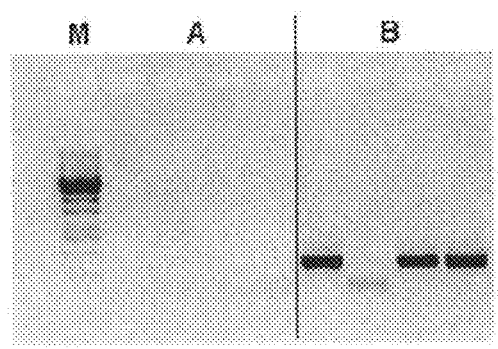

The result is shown in FIG. 10: M: marker—DNA ladder; A: untreated toothpick used for the transfer of soybean leaf material into the PCR; four samples; B: toothpick coated with heparin/Tween® used for the transfer of soybean leaf material into the PCR; four samples Conclusion:

The use of heparin-coated toothpicks for the transfer of soybean leaf material into the PCR improves the amplificate formation as compared to the use of untreated toothpicks.

Example 11: Soybean, Wheat, Maize, Tobacco: Tool Treated, Simple Controls

Sample material: Leaves from Arabidopsis, wheat, soybean, maize, tobacco

Description of tool (kind and amount of active substances and auxiliary agents): Plastic toothpick treated with 38 IU heparin/ml of 10% Tween®20 solution.

Figure 11:
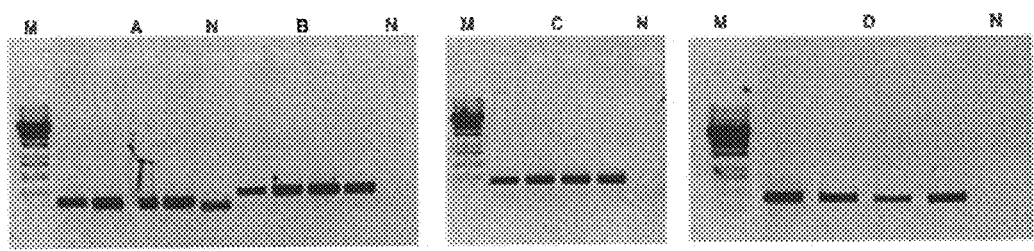

Primer: Primer pair #7 for soybean, primer pair #8 for maize, primer pair #9 for wheat, primer pair #10 for tobacco PCR program: #1 for wheat and tobacco. #4 for soybean and maize The result is shown in FIG. 11: M—marker (1× per gel); N—negative control (no template control, 1× for each plant species); A—soybean (4×); B—maize (4×); C—wheat (4×); D—tobacco (4×)

Conclusion:

The use of heparin-coated toothpicks for the transfer of leaf material from soybean, maize, wheat and tobacco, amplificates can be produced in PCR using plant species-specific primers.

Example 12 Arabidopsis, Sampling, Piercing, Scratching

Figure 12:
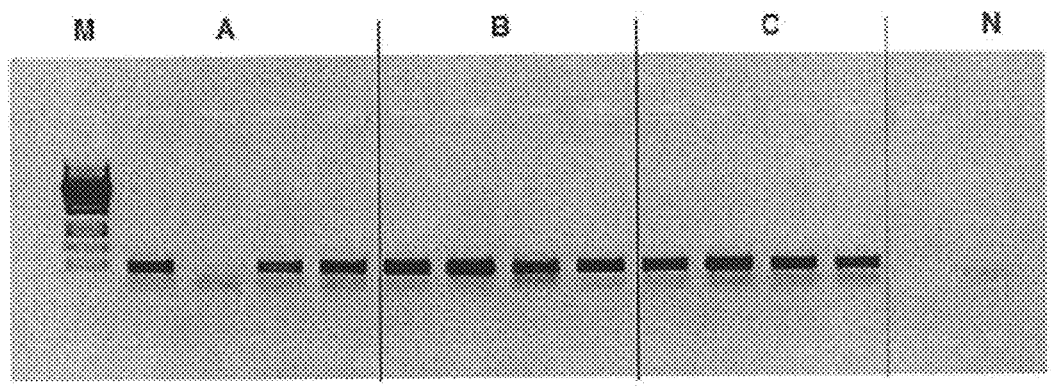

Sample material: Arabidopsis leaves
Description of tool (kind and amount of active substances and auxiliary agents): Plastic toothpick treated with 38 IU heparin/ml of 10% Tween®20 solution
Primer: Primer pair #11
PCR program: #5
The result is shown in FIG. 12: M: marker, DNA ladder; A: old leaves pierced with heparin-treated toothpick for sample uptake; B: young leaves scratched with heparin-treated toothpick for sample uptake; C: young leaves pierced with heparin-treated toothpick for sample uptake; N: negative control (no sample added)
Conclusion:
Using heparin-treated toothpicks, samples can be transferred into PCR and then successfully amplified from young and old Arabidopsis leaves. The plant leaf sample can be taken up both by piercing the leaf and by scratching the leaf.

Figure 13:
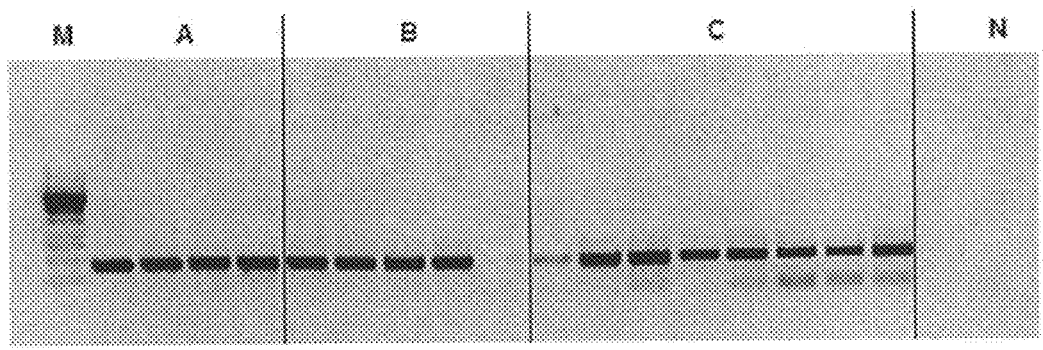

Example 13: Tobacco, Sampling: Pricking, Scratching, Duration of Sample Transfer: 0-4 s Sample material: Tobacco leaves
Description of tool (kind and amount of active substances and auxiliary agents): Plastic toothpick treated with 38 IU heparin/ml of 10% Tween®20 solution
Primer: Primer pair #10
PCR program: #1
The result is shown in FIG. 13: M: marker, DNA ladder; A: leaves pricked with heparin-treated toothpick, then immediately transfer into PCR; B: leaves pricked with heparin-treated toothpick, then waiting for four seconds, then transfer into PCR; C: leaves scratched with heparin-treated toothpick, then waiting for four seconds, then transfer into PCR; N: negative control (no sample added)
Conclusion:
Using heparin-treated toothpicks, samples can be transferred into PCR and then successfully amplified from tobacco leaves. After having been taken up with the toothpick by pricking the leaf, the plant leaf sample can be transferred to PCR immediately (about one second) or after a waiting time of 4 s, and yields amplificates.

Figure 14:
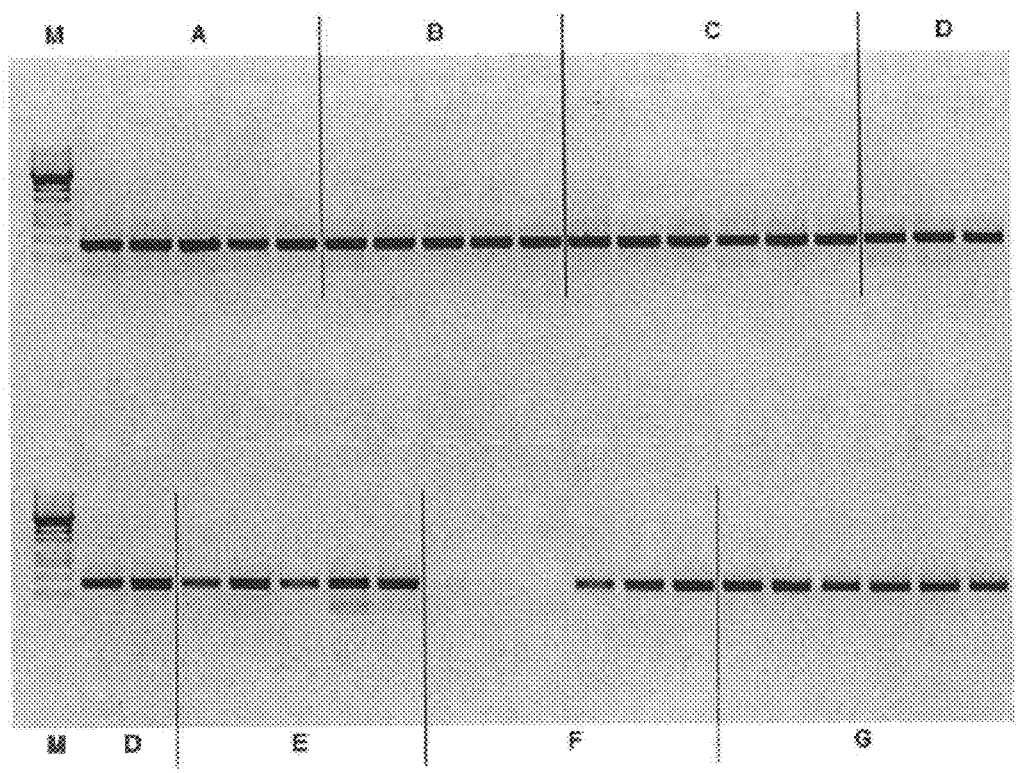

Example 14: Tobacco, Sampling and Transfer: Pricking, Scratching, 1×, 2× Dipping Stirring in Sample material: Tobacco leaf
Description of tool (kind and amount of active substances and auxiliary agents): Plastic toothpick treated with 38 IU heparin/ml of 10% Tween®20 solution
Primer: Primer pair #10
PCR program: #1
The result is shown in FIG. 14: M: marker, DNA ladder; A: prick leaf→, Immediate transfer (dipping once) to the PCR; B: prick leaf→transfer to the PCR after 4 s; C: prick leaf→immediately dipping 2× into the PCR; D: prick leaf→immediately stirring into the PCR; E: scratch leaf→immediately dipping into the PCR; F: scratch leaf→immediately dipping 2× into the PCR; G: scratch leaf→immediately stirring into the PCR
Conclusion:
Using heparin-treated toothpicks, samples can be transferred into PCR and then successfully amplified from tobacco leaves. After pricking the tobacco leaf, the toothpick can be dipped into the PCR Immediately or after 4 s; the sample can be transferred from the toothpick by dipping the tip into the PCR once or twice, or by stirring in. Scratching the leaf surface in part leads to failing amplification, probably because less plant material sticks to the tip when scratching as compared to pricking.

Example 15: Mechanical Stability of the Coating, Tobacco

Figure 15:
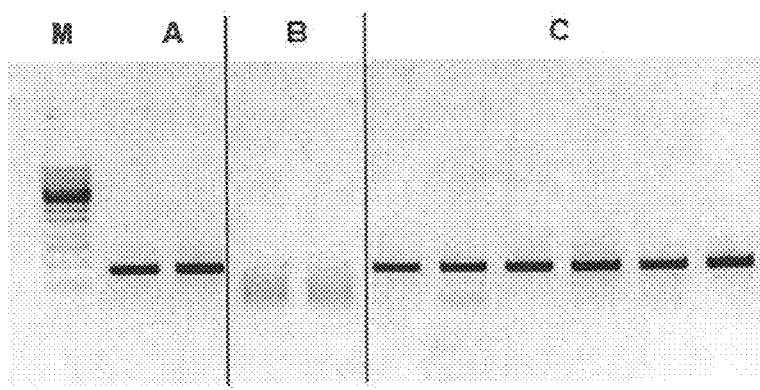

Sample material: Tobacco leaf
Description of tool (kind and amount of active substances and auxiliary agents): Plastic toothpick treated with 38 IU heparin/ml of 10% Tween®20 solution
Primer: Primer pair #10
PCR program: #1
The result is shown in FIG. 15: M: marker, DNA ladder; A: heparin-coated toothpicks used for sample transfer, fresh, without shaking; B: uncoated toothpicks used for sample transfer; C: heparin-coated toothpick shaken before using it in a package (plastic bag in a cardboard box) (simulation of shipping)
Conclusion:
Heparin-treated toothpicks keep their functionality as inhibitor-inactivating sample transfer tools even if they are previously shaken in a plastic bag for some time (simulation of shipping).

Example 16: Duplex PCR Tobacco-Grape Vine, Bioanalyzer

Figure 16:
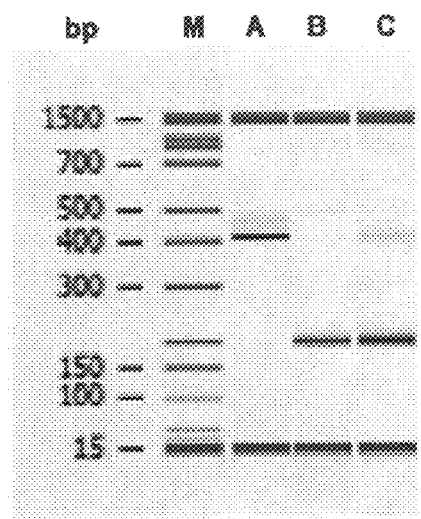

Sample material: Leaf from tobacco, grape vine
Description of tool (kind and amount of active substances and auxiliary agents): Plastic toothpick treated with 38 IU heparin/ml of 10% Tween®20 solution
Primer: Primer pair #10; Primer pair #12
PCR program: #1
The result is shown in FIG. 16: M—marker; A—duplex PCR mix; template: tobacco; B—duplex PCR mix; template: vine leaves; C—duplex PCR; template: tobacco+vine leaves
Conclusion:
With the tool, it is also possible to transfer sample material from two different plants by successively pricking into PCR, and amplify them successfully.

Example 17: Soybean, Cotton, Wheat, Amplicon 418 bp

Figure 17:
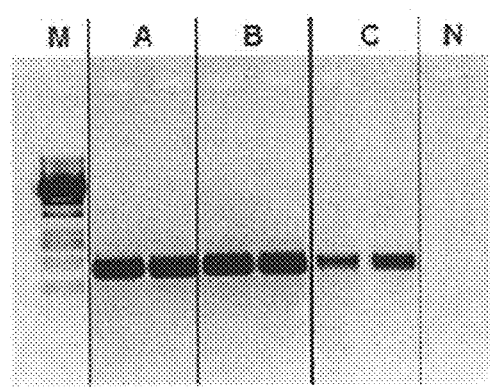

Sample material: Leaf from soybean, cotton, wheat
Description of tool (kind and amount of active substances and auxiliary agents): Plastic toothpick treated with 38 IU heparin/ml of 10% Tween®20 solution
Primer: Primer pair #13
PCR program: #6
The result is shown in FIG. 17: M—marker; A—soybean; B—cotton; C—wheat; N—negative control (no sample added)
Conclusion:
When sample material is transferred using the tool, a 418 bp product can be successfully amplified from soybean, cotton and wheat leaf material.

Example 18: Cotton, Wheat, Amplicon 745 bp

Figure 18:
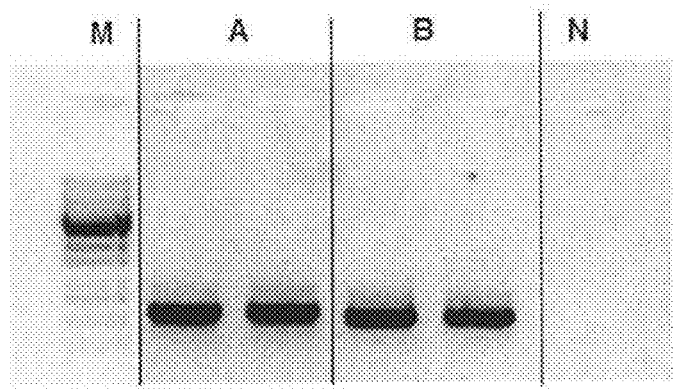

Sample material: Leaves from cotton and wheat
Description of tool (kind and amount of active substances and auxiliary agents): Plastic toothpick treated with 38 IU heparin/ml of 10% Tween®20 solution
Primer: Primer pair #14
PCR program: #7
The result is shown in FIG. 18: M: marker, DNA ladder; A: cotton; B: wheat; N: negative control (no template control)
Conclusion:
After transfer of cotton and wheat leaf material into PCR using the tool, it is possible to amplify a 745 bp DNA fragment.

Figure 19:
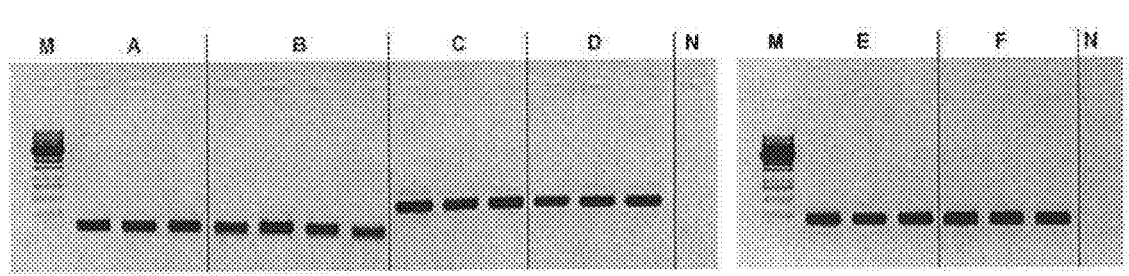

Example 19: Tobacco, Vine Leaves: After Sampling, Direct Sample Transfer Vs. Drying of Sample Sample material: Leaf material from soybean, tobacco, grape vine
Description of tool (kind and amount of active substances and auxiliary agents): Plastic toothpick treated with 38 IU heparin/ml of 10% Tween®20 solution
Primer: Primer pair #7 for soybean, primer pair #10 for tobacco, primer pair #12 for grape vine
PCR program: #7 for tobacco, grape vine; #8 for soybean
The result is shown in FIG. 19: M: marker, DNA ladder; A: soybean. Direct sample transfer after uptake of the sample onto the tool; B: soybean. Sample dried onto the tool: After uptake of the sample onto the tool, it was dried in air for 1.5 h. Only after that the tool tip touched the PCR; C: tobacco. Direct sample transfer after uptake of the sample onto the tool; D: tobacco. Sample dried onto the tool: After uptake of the sample onto the tool, it was dried in air for 1.5 h. Only after that the tool tip touched the PCR; E: vine leaves. Direct sample transfer after uptake of the sample onto the tool; F: vine leaves, Sample dried onto the tool: After uptake of the sample onto the tool, it was dried in air for 1.5 h. Only after that the tool tip touched the PCR; N—negative control (no sample added).
Conclusion:
After uptake of plant leaf material onto the tool, the tool may be stored for 1.5 h before the sample material is transferred from the tool into the PCR, without the functionality being adversely affected.

Example 20: Duplex PCR Soybean Cotton, Wheat, 418 bp+757 bp

Figure 20:
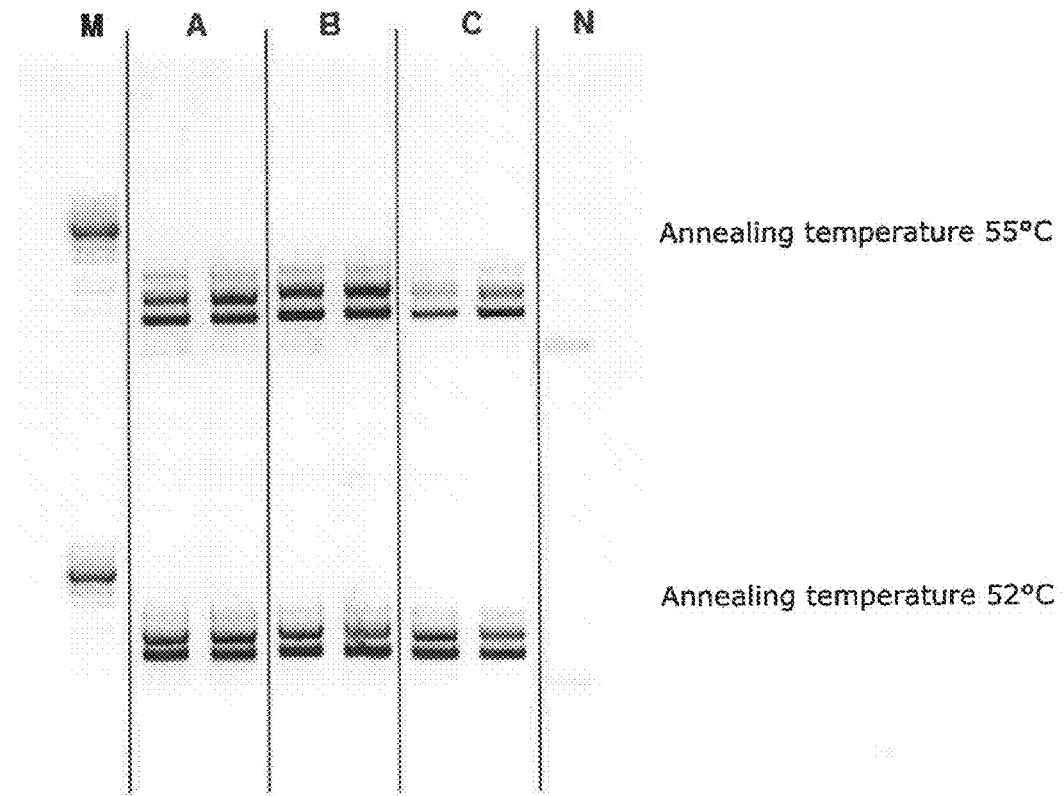

Sample material: Leaf material from soybean, cotton, wheat
Description of tool (kind and amount of active substances and auxiliary agents): Plastic toothpick treated with 38 IU heparin/ml of 10% Tween®20 solution
Primer: Primer mix #15
PCR program: #7 (annealing at 55° C.); #11 (annealing at 52° C.)
The result is shown in FIG. 20: M: marker, DNA ladder; A: soybean; B: cotton; C: wheat; N: negative control (no sample added)
Conclusion:
Using the transfer tool, it is possible to subsequently perform duplex PCRs, and to amplify both a 418 bp fragment and a 757 bp fragment from plant leaf material in one PCR.

Example 21: Sampling: Pricking Vs. Piercing, Tobacco, Grape Vine

Figure 21:
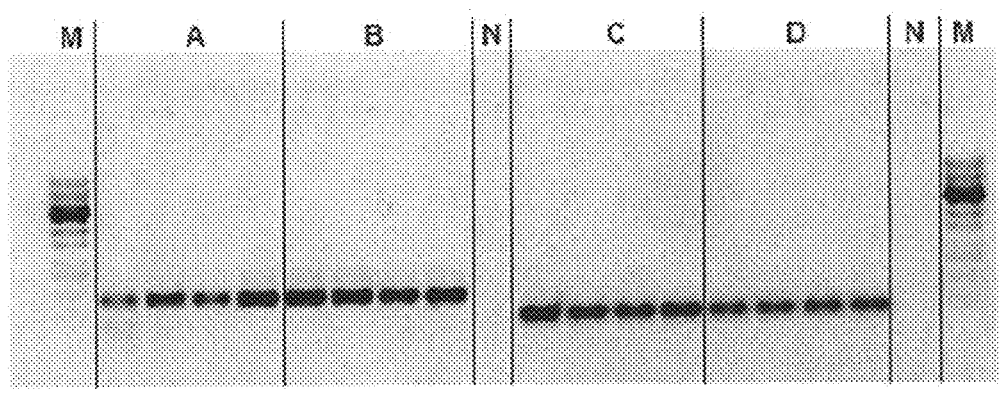

Sample material: Leaves from tobacco and grape vine
Description of tool (kind and amount of active substances and auxiliary agents): Plastic toothpick treated with 38 IU heparin/ml of 10% Tween®20 solution
Primer: Primer pair #10 tobacco, Primer pair #12 Wein
PCR program: #9
The result is shown in FIG. 21: M: marker, DNA ladder; A: tobacco. Pricking—the leaf is lying on a solid substrate, and the transfer tool is used for pricking into the leaf; B: tobacco. Piercing—the leaf is pierced with the tool over about 5-10 mm; C: grape vine. Pricking—the leaf is lying on a solid substrate, and the transfer tool is used for pricking into the leaf; D: grape vine. Piercing—the leaf is pierced with the tool over about 5-10 mm; N: negative control (no sample added)
Conclusion:
Using the sample transfer tool, sample material can be taken up from a plant leaf by pricking into the leaf while it is lying on a solid substrate, or by piercing it over 5-10 mm.

Example 22: Coating Procedure Individually or in Bunches

Figure 22:
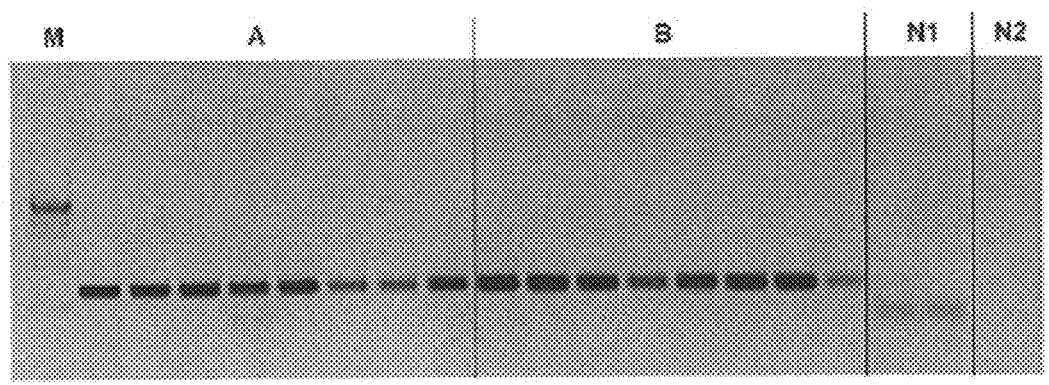

Sample material: Leaf from tobacco that was stored at about 4° C. in a refrigerator for about 1.5 months prior to use
Description of tool (kind and amount of active substances and auxiliary agents): Plastic toothpick treated with 38 IU heparin/ml of 10% Tween®20 solution
Primer: Primer pair #10
PCR program: #1
The result is shown in FIG. 22: M: marker, DNA ladder; A: toothpicks were coated individually; B: toothpicks were coated as a bunch of 100 pieces. From the bunch, toothpicks were used for sample transfer for testing from the middle and from the edge. N1: Negative control 1—uncoated toothpicks used for sample transfer; N2: negative control 2 (no template control)
Conclusion:
Toothpick can be coated with heparin/surfactant both individually and in bunches of 100 pieces, to arrive at the functionality of the inhibitor-inactivating sample transfer tool.

Example 23 Comparison: Lysate Vs. Direct Sample Transfer. Tobacco, Cotton

Figure 23:
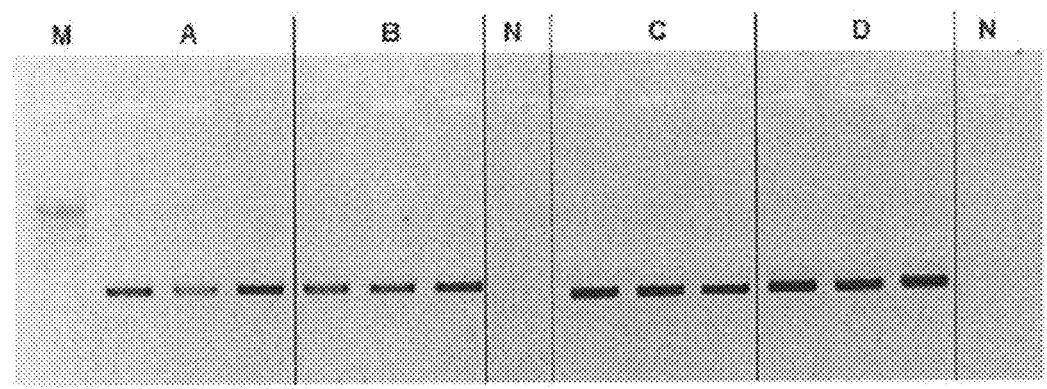

Sample material: Leaf from tobacco and cotton directly, or a lysate thereof (lysate preparation: 20 µl lysis buffer+0.5 µl proteinase K+1 mm diameter punched piece of leaf, incubation at room temperature for 3 min, incubation at 98° C. for 3 min).
Description of tool (kind and amount of active substances and auxiliary agents): Plastic toothpick treated with 38 IU heparin/ml of 10% Tween®20 solution
Primer: Primer pair #10 for tobacco (422 bp amplificate), primer pair #5 for cotton (308 bp amplificate)
PCR program: #1
The result is shown in FIG. 23: M: marker; A: tobacco, sample transfer with treated sample transfer tool; B: tobacco; lysate preparation with lysis buffer and proteinase, then transfer of 1 µl thereof into the PCR; N: negative control (no template control); C: cotton; sample transfer with treated sample transfer tool; D: cotton; lysate preparation with lysis buffer and proteinase, then transfer of 1 µl thereof into the PCR; N: negative control (no template control)

Conclusion:

When the transfer tool coated with the active substance is used, the PCR can proceed just as successfully as when a plant leaf lysate is used as the sample material.

Example 24: PCR Volume 10-50 µl Tobacco, Cotton

Figure 24:
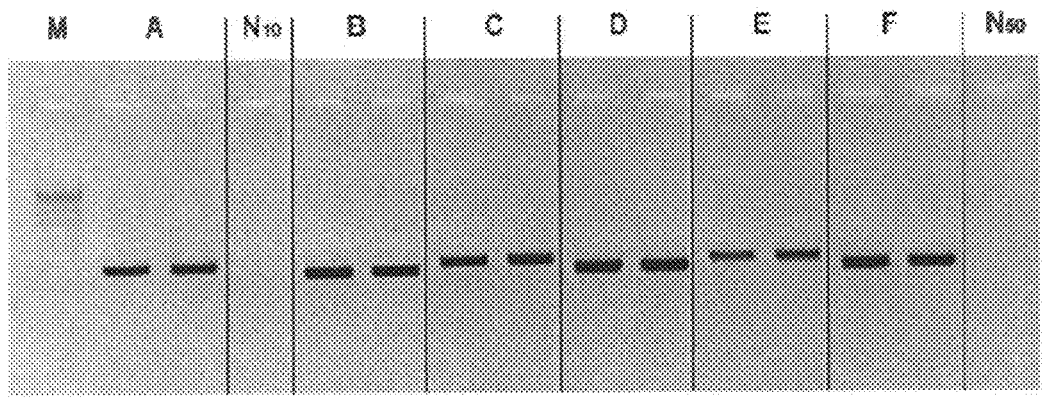

Sample material: Leaves from cotton, tobacco
Description of tool (kind and amount of active substances and auxiliary agents): Plastic toothpick treated with 38 IU heparin/ml of 10% Tween®20 solution
Primer: Primer pair #10 for tobacco, primer pair #5 for cotton
PCR program: #1
The result is shown in FIG. 24: M: marker, DNA ladder; A: PCR volume 10 µl; tobacco; N10: PCR volume 10 µl, negative control (no sample added); B: PCR volume 10 µl; cotton; C: PCR volume 20 µl, tobacco; D: PCR volume 20 µl, cotton; E: PCR volume 50 µl; tobacco; F: PCR volume 50 µl; cotton; N50: PCR volume 50 µl, negative control (no sample added)

Conclusion:

Sample transfer tools coated with the active substance can be used to transfer sample material into PCRs containing 10 µl-50 µl volumes, and thus enable a successful amplification of the target products.

Example 25: Storage of Coating: Fresh Vs. 2 Months at −20° C. to +37° C.

Figure 25:
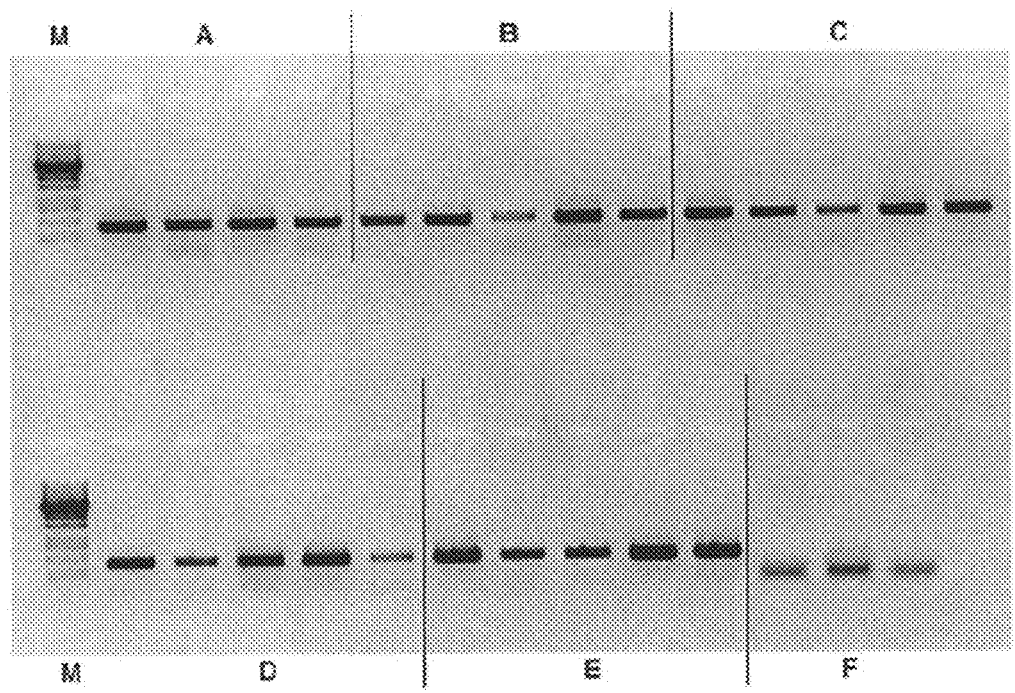
Figure 26A:
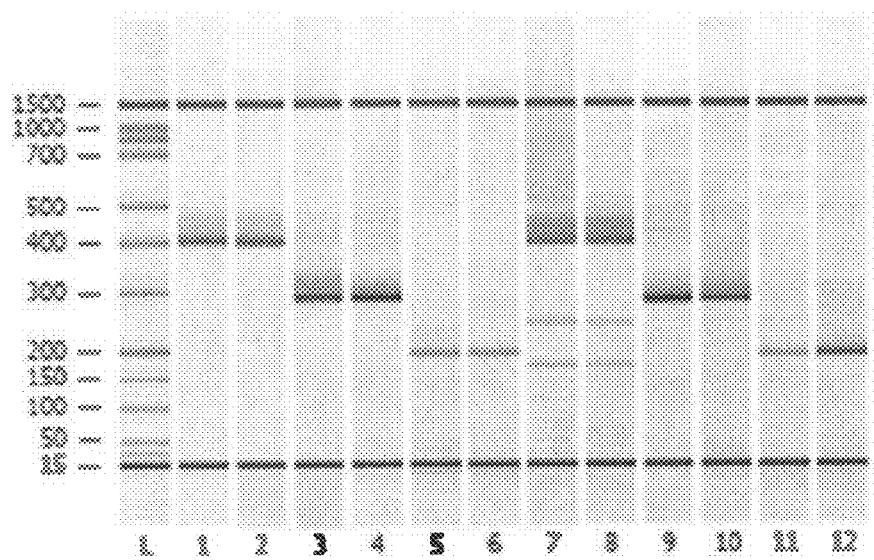
Figure 26B:
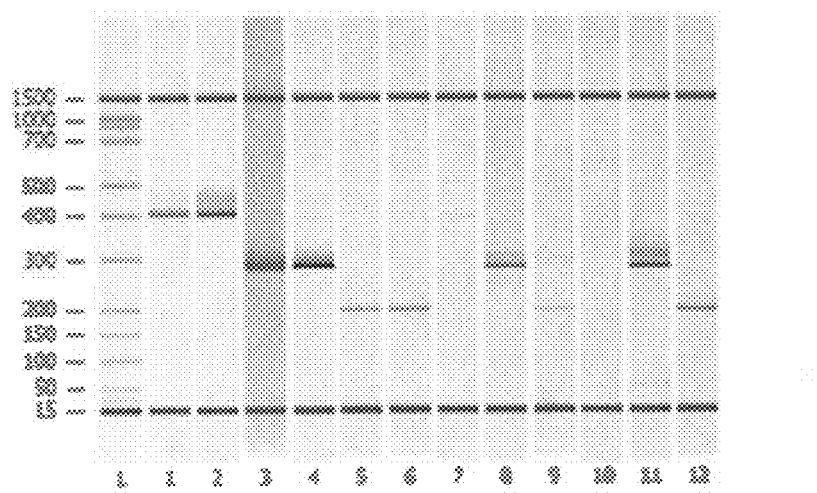
Figure 26C:
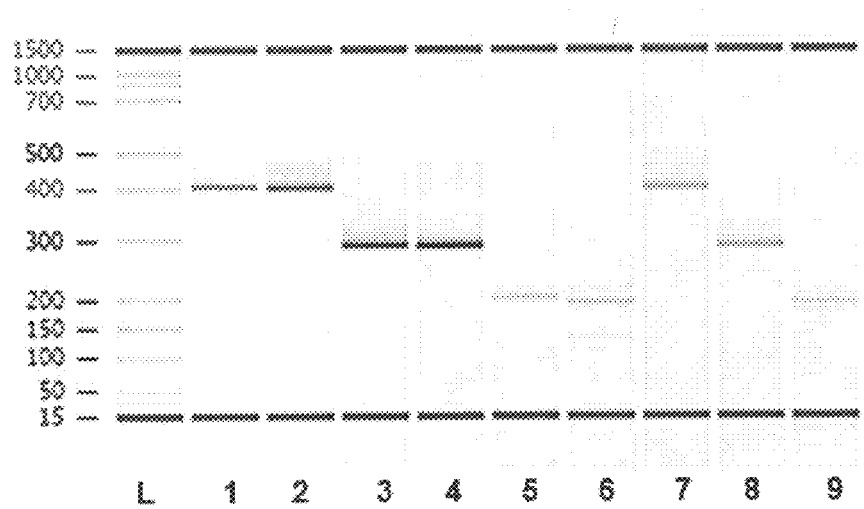
Figure 26D:
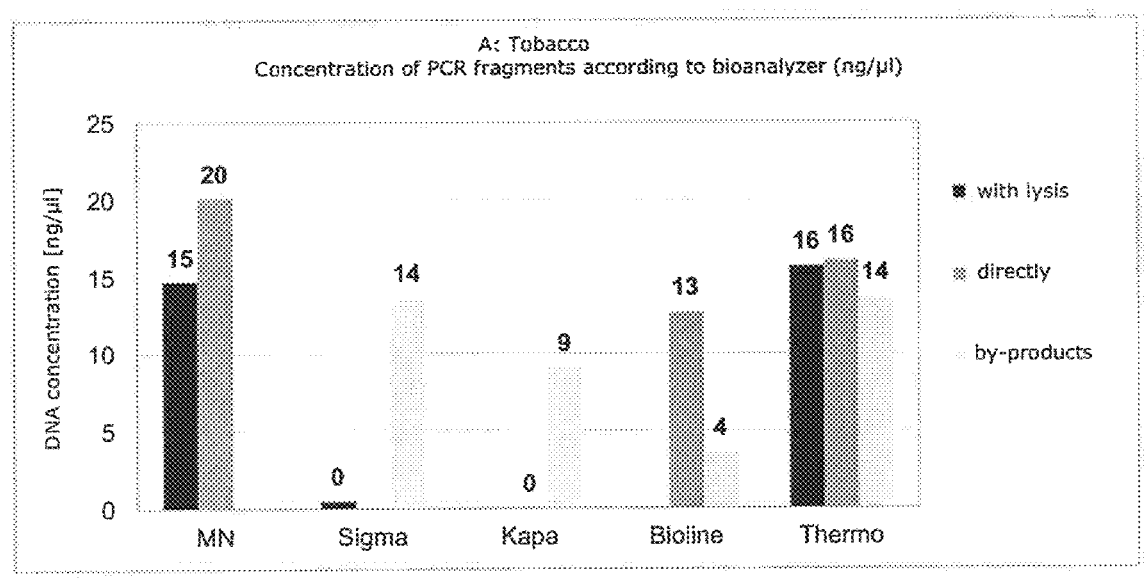
Figure 26E:
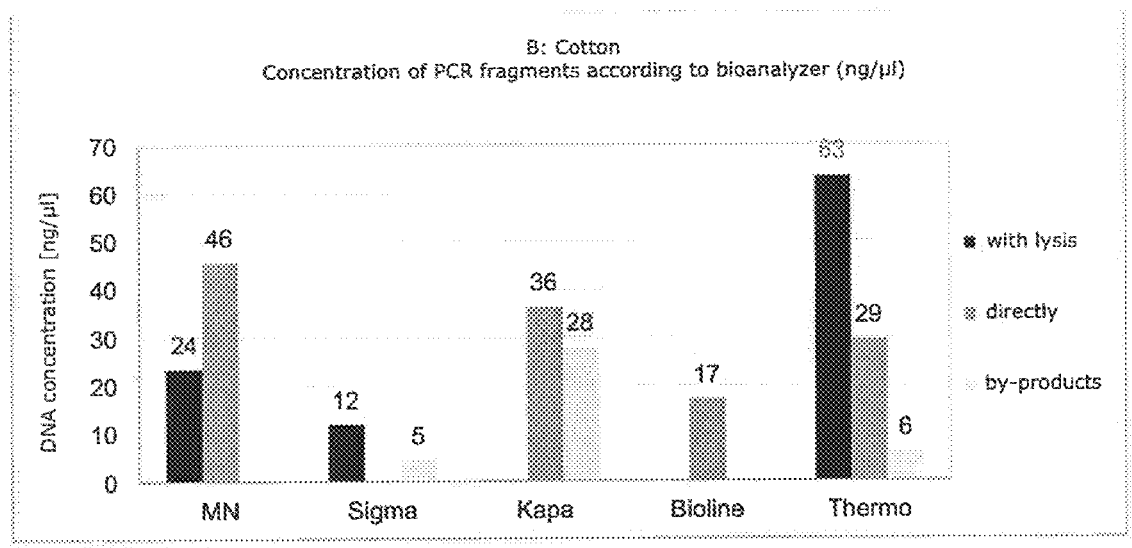
Figure 26F:
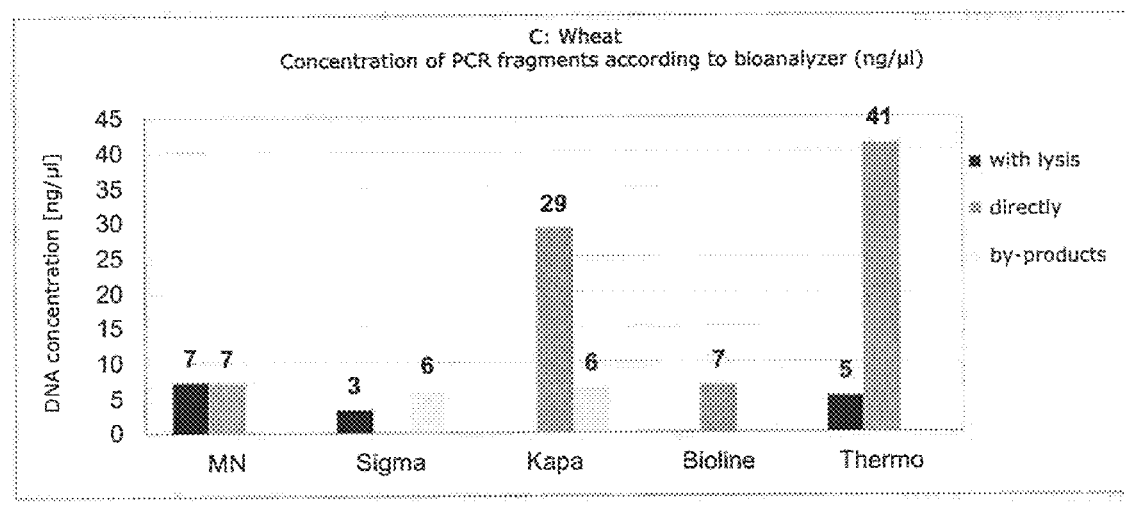

Sample material: Leaf from tobacco
Description of tool (kind and amount of active substances and auxiliary agents): Plastic toothpick treated with 38 IU heparin/ml of 10% Tween®20 solution
Primer: Primer pair #10
PCR program: #12
The result is shown in FIG. 25: M: marker, DNA ladder; A: use of freshly prepared transfer tools; B: use of coated transfer tools stored at RT for 2 months; C: use of coated transfer tools stored at 37° C. for 2 months; D: use of coated transfer tools stored at 4° C. for 2 weeks; E: use of coated transfer tools stored at −20° C. for 2 weeks; F: use of uncoated toothpicks Conclusion:

The transfer tools coated with heparin/surfactant are stable for at least 2 months when stored at 37° C. and thereafter can be used as inhibitor-inactivating sample transfer tools.

Example 26: Comparison of Products

Sample material: Leaves from wheat, tobacco, cotton
Description of tool (kind and amount of active substances and auxiliary agents): Plastic toothpick treated with 38 IU heparin/ml of 10% Tween®20 solution
Primer: Primer pair #9 for wheat, primer pair #10 for tobacco, primer pair #5 for cotton
PCR program in Eppendorf Gradient Cycler: MN: PCR program #1; Thermo Scientific: #13; Sigma: #14; Bioline: #15; KAPA: #16
The result is shown in FIGS. 26 a-f. The following procedures/products were compared: MN, simple sample preparation by fast lysis; MN, process according to the invention using sample transfer tool; Thermo Scientific Phire Plant Direct PCR, dilution protocol; Thermo Scientific Phire Plant Direct PCR, direct protocol, sample transfer by biopsy punch; Sigma Extrac-N-Amp Plant PCR, simple sample preparation by fast lysis; Bioline MyTaq Plant PCR, direct protocol; KAPA3G Plant PCR, direct protocol All procedures/kits were tested with leaves from wheat, tobacco and cotton.

The performance of the sample preparation by fast lysis was effected as follows: 20 µl of lysis buffer containing Tris, KCl and a non-ionic detergent)+0.5 µl of proteinase K solution (20 mg/ml)+about 1 mm² leaf disk, shaking at room temperature for 2 min, incubate at 98° C. for 3 min. From this, 1 µl was then added to the PCR as a template.

The performance with the products from Thermo, Sigma, Bioline and Kapa was effected in accordance with the manufacturer's instructions. The amplificates were examines using a Bioanalyzer.

Comparison against Thermo Scientific Phire Plant Direct PCR (FIG. 26 a)
L: DNA ladder
1: MN, tobacco, sample preparation by fast lysis
2: MN, tobacco, use of the sample transfer tool according to the invention
3: MN, cotton, sample preparation by fast lysis
4: MN, cotton, use of the sample transfer tool according to the invention
5: MN, wheat, sample preparation by fast lysis
6: MN, wheat, use of the sample transfer tool according to the invention
7: Thermo, tobacco, dilution protocol
8: Thermo, tobacco, sample transfer using biopsy punch
9: Thermo, cotton, dilution protocol
10: Thermo, cotton, sample transfer using biopsy punch
11: Thermo, wheat, dilution protocol
12: Thermo, wheat, sample transfer using biopsy punch Conclusion:

In all cases, the target fragments (422 bp, 308 bp, 201 bp) were amplified. The process according to the invention (lanes 2, 4, 6, use of the sample transfer tool) is advantageous over the method of Thermo Scientific Phire Plant Direct PCR, direct protocol, sample transfer using a biopsy punch, because no biopsy punch needs to be used and purified/decontaminated, and in addition, less by-products are formed.

Comparison against Sigma Extrac-N-Amp Plant PCR and KAPA3G Plant PCR, direct protocol (FIG. 26 b)
L: DNA ladder
1: MN, tobacco, sample preparation by fast lysis
2: MN, tobacco, use of the sample transfer tool according to the invention
3: MN, cotton, sample preparation by fast lysis
4: MN, cotton, use of the sample transfer tool according to the invention
5: MN, wheat, sample preparation by fast lysis
6: MN, wheat, use of the sample transfer tool according to the invention
7: Sigma, tobacco, simple sample preparation by fast lysis
8: Sigma, cotton, simple sample preparation by fast lysis
9: Sigma, wheat, simple sample preparation by fast lysis
10: Kapa, tobacco, sample transfer using biopsy punch
11: Kapa, cotton, sample transfer using biopsy punch
12: Kapa, wheat, sample transfer using biopsy punch Conclusion:

In most cases, the target fragments (422 bp, 308 bp, 201 bp) were amplified. The process according to the invention (lanes 2, 4, 6, use of the sample transfer tool) is advantageous over the method of Sigma and Kapa because the 422 bp product is also formed, while it is not formed with the Sigma and Kapa kit (lanes 7, 10). Further, the process according to the invention is advantageous over the other two kits because either no biopsy punch needs to be used and purified/decontaminated, or no lysate needs to be prepared.

Comparison against Bioline MyTaq Plant PCR, direct protocol (FIG. 26 c)
L: Marker
1: MN, tobacco, sample preparation by fast lysis
2: MN, tobacco, use of the sample transfer tool according to the invention
3: MN, cotton, sample preparation by fast lysis
4: MN, cotton, use of the sample transfer tool according to the invention
5: MN, wheat, sample preparation by fast lysis
6: MN, wheat, use of the sample transfer tool according to the invention
7: Bioline, tobacco,
8: Bioline, cotton,
9: Bioline, wheat.
Conclusion:
In all cases, the target fragments (422 bp, 308 bp, 201 bp) were amplified. The process according to the invention (lanes 2, 4, 6, use of the sample transfer tool) is advantageous over the Bioline method because no biopsy punch needs to be used and purified/decontaminated, and more target product was formed.

The quantitative evaluation of the formed amplificates is represented in the following drawings.

Drawing: FIG. 26 d tobacco; FIG. 26 e cotton; FIG. 26 f wheat:

Legend: MN, black bar: lysis protocol; MN, gray bar: use of the inhibitor-inactivating sample transfer tool; Sigma: Sigma Extrac-N-Amp Plant PCR Kit;

Kapa: KAPA3G Plant PCR Kit; Bioline: Bioline MyTaq Plant PCR Kit; Thermo: Thermo Scientific Phire Plant Direct PCR Kit Bar: black: lysis protocol; gray: direct=direct transfer of leaf material into the PCR; light gray: by-products
Conclusion:
The process according to the invention (MN, direct) provides higher yields of target fragment in the majority of cases as compared to the competing processes. Further, less detectable by-products (amplificates having sizes other than the target sizes) are obtained in the process according to the invention.

Examples Group III: Other Kinds of Samples

Example 27: Avocado Flesh: Tool+/−Heparin

Figure 27:
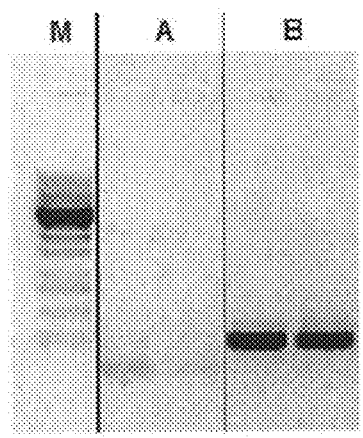

Sample material: Flesh from avocado
Description of tool (kind and amount of active substances and auxiliary agents): Plastic toothpick treated with 38 IU heparin/ml of 10% Tween®20 solution
Primer: Primer pair #5
PCR program: #1
The result is shown in FIG. 27: M: marker, DNA ladder; A: untreated toothpicks used for sample transfer; B: using inhibitor-inactivating sample transfer tool
Conclusion:
When the toothpick (sample transfer tool) coated with the active substance is used for the transfer of avocado flesh as the sample material into the PCR, a well recognizable target product is formed, whereas when untreated toothpicks are used, no amplificate worth mentioning is formed. Thus, the process according to the invention can be used advantageously not only for blood and plant leaf materials, but also for avocado flesh.

Example 28: Avocado Flesh: Tool+/−Heparin

Figure 28:
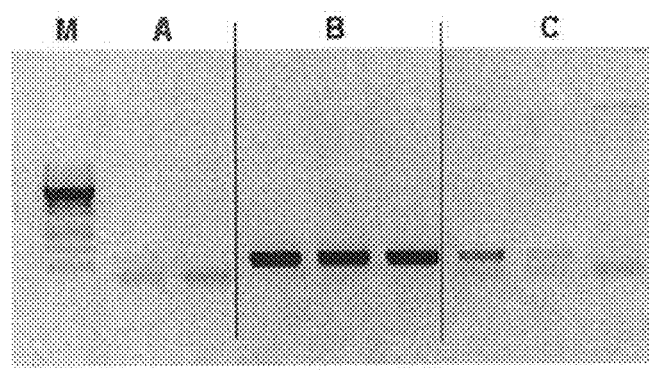

Sample material: Flesh from avocado
Description of tool (kind and amount of active substances and auxiliary agents): Plastic toothpick treated with 38 IU heparin/ml of 10% Tween®20 solution
Primer: Primer pair #5
PCR program: #1
The result is shown in FIG. 28: M: marker, DNA ladder; A: use of untreated toothpicks for sample transfer; B: use of treated toothpicks for sample transfer. The avocado flesh was briefly pricked; C: use of treated toothpicks for sample transfer. The avocado flesh was briefly pricked, and scratched over the surface.
Conclusion:
Conclusion: When the toothpick (sample transfer tool) coated with the active substance is used for the transfer of avocado flesh as the sample material into the PCR, a well recognizable target product is formed, whereas when untreated toothpicks are used, no amplificate worth mentioning is formed. If the sample material is not only pricked, but also scratched over the surface with the sample transfer tool, less or no target product is formed, which is to be attributed to the larger amount of transferred sample material.

Examples Group IV: Different Active Substances

Figure 29:
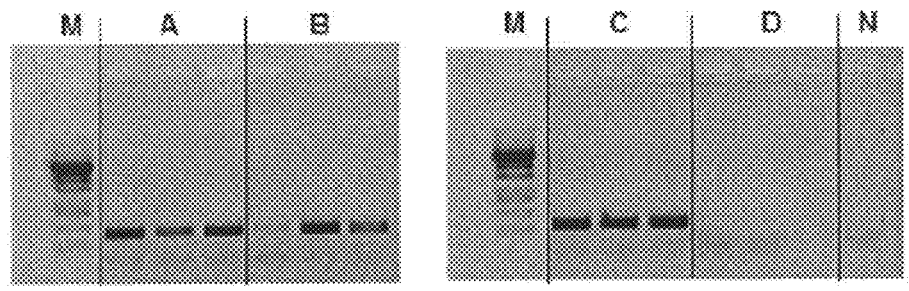

Example 29: Chondroitin Sulfate 5%, 1% as Compared to Heparin and Negative Control Sample material: EDTA-treated mouse blood
Description of tool (kind and amount of active substances and auxiliary agents): Plastic toothpick coated with: A: 5% and B: 1% solution of chondroitin sulfate sodium salt (CAS 9082-07-9) in a 10% Tween®20 solution; C: 20 IU heparin/ml of 10% Tween®20 solution
Primer: Primer pair #2
PCR program: #2
The result is shown in FIG. 29: M: marker, DNA ladder; transfer of the sample with toothpick coated with: A: 5% solution of chondroitin sulfate sodium salt in a 10% Tween®20 solution, B: 1% solution of chondroitin sulfate sodium salt in a 10% Tween®20 solution, C: 20 IU heparin per ml of 10% Tween®20 solution, D: uncoated toothpick, N: negative control (no template control)

Conclusion

Not only heparin, but also chondroitin sulfate is suitable for preparing a functional inhibitor-inactivating sample transfer tool.

Example 30: Dextran Sulfate 0.1-5% as Compared to Heparin Control and NK, Mouse EDTA Blood Sample material: EDTA-treated mouse blood
Description of tool (kind and amount of active substances and auxiliary agents): Plastic toothpick coated with a solution of 5% chondroitin sulfate or 5%, 3%, 1%, 0.5%, 0.1% dextran sulfate (CAS 9011-18-1) in 10% Tween®20 solution. Plastic toothpick treated with 38 IU heparin/ml of 10% Tween®20 solution.

Primer: Primer pair #2

PCR program: #2

Figure 30:
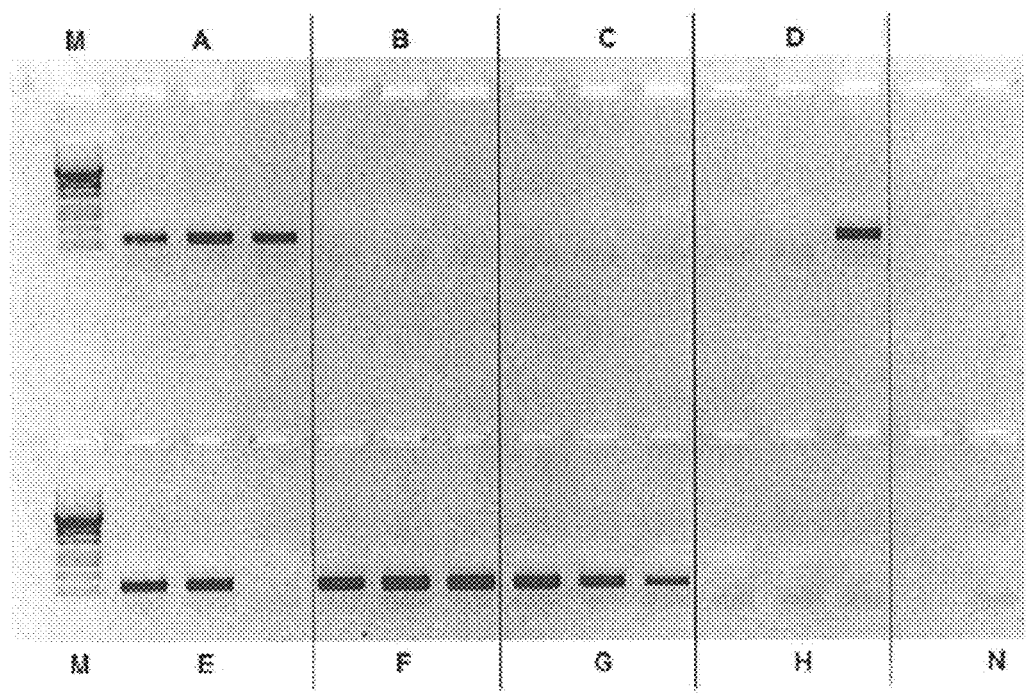
Figure 31:
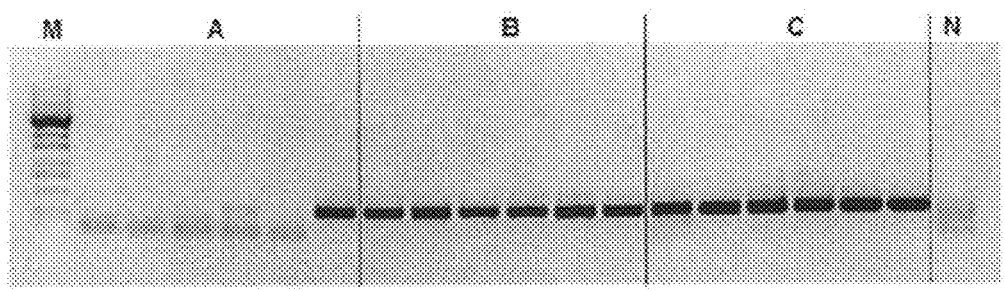
Figure 31:
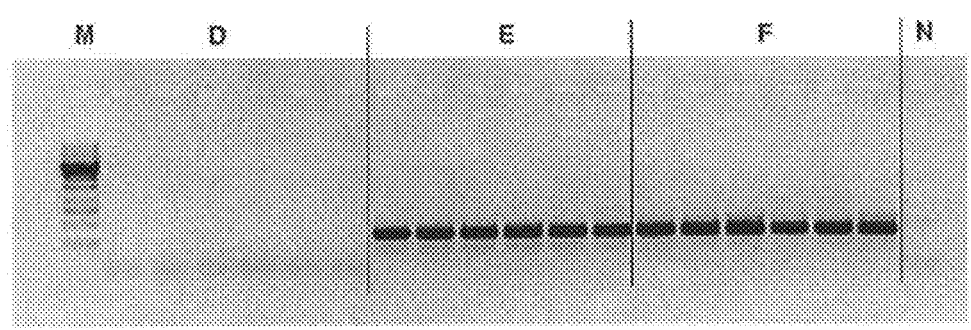

The result is shown in FIG. 30: M: marker, DNA ladder; transfer of the sample with toothpick coated with: A: 5% solution of chondroitin sulfate sodium salt in 10% Tween®20 solution, B: 5% solution of dextran sulfate in 10% Tween®20 solution, C: 3% solution of dextran sulfate in 10% Tween®20 solution, D: 1% solution of dextran sulfate in 10% Tween®20 solution, E: 0.5% solution of dextran sulfate in 10% Tween®20 solution, F: 0.1% solution of dextran sulfate in 10% Tween®20 solution, G: 20 IU heparin/ml in 10% Tween®20 solution, H: negative control (uncoated toothpick), N: negative control (no template control)

Conclusion:

Toothpicks coated with a 0.1-0.5% solution of dextran sulfate can be used as functional inhibitor-inactivating sample transfer tools (E, F), which also holds for toothpicks coated with chondroitin sulfate sodium salt (A) or heparin (G). In contrast, sample transfer with untreated toothpicks does not result in successful amplification (H).

Example 31: Solution of Chaotropic Salt Instead of Heparin

Sample material: Cress leaf pulp, prepared by triturating 1 mass part of cress leaves with 1 mass part of water Description of tool (kind and amount of active substances and auxiliary agents): Plastic toothpicks treated with a solution of 6 M guanidine hydrochloride (CAS 50-01-01), 90 mm EDTA (CAS 60-00-4), 1.5% Tween®20, 50 mm Tris-Cl pH 8) as well as plastic toothpicks treated with 38 IU heparin/ml in 10% Tween®20 solution Primer: Primer pair #5 for a 308 bp target; primer pair #5 for a 447 bp target.

PCR program: #2

The result is shown in FIG. 30:

Upper part of Figure: Primer pair #5, 308 bp amplificate: M: marker; A: untreated toothpicks for sample transfer; B: heparin-treated toothpicks for sample transfer; C: toothpick treated with chaotropic salt solution for sample transfer; N: negative control (no template control)

Lower part of Figure: Primer pair #5, 447 bp amplificate: M: marker; D: untreated toothpicks for sample transfer; E: heparin-treated toothpicks for sample transfer; F: toothpick treated with chaotropic salt solution for sample transfer; N: negative control (no template control)

Conclusion:

An inhibitor-inactivating effect can be produced for cress leaf pulp not only by coating a sample transfer tool with heparin, but also by coating it with a solution of a chaotropic salt.

Note: The mechanism of action can be the same or different for heparin and a solution of a chaotropic salt. It is to be considered that heparin binds and thereby inactivates inhibitors in samples. Chaotropic salts either inhibit inhibitors by their denaturing effect, or they may support DNA release by their denaturing and lysis-promoting effect.

Example 32: Carrageenan 0.05-0.5%, Rabbit Blood

Sample material: EDTA-treated rabbit blood

Description of tool (kind and amount of active substances and auxiliary agents): Plastic toothpick coated with 0.5% or 0.1% or 0.05% A-carrageenan (CAS 9064-57-7) in water Primer: Primer pair #1

PCR program: #2

Figure 32:
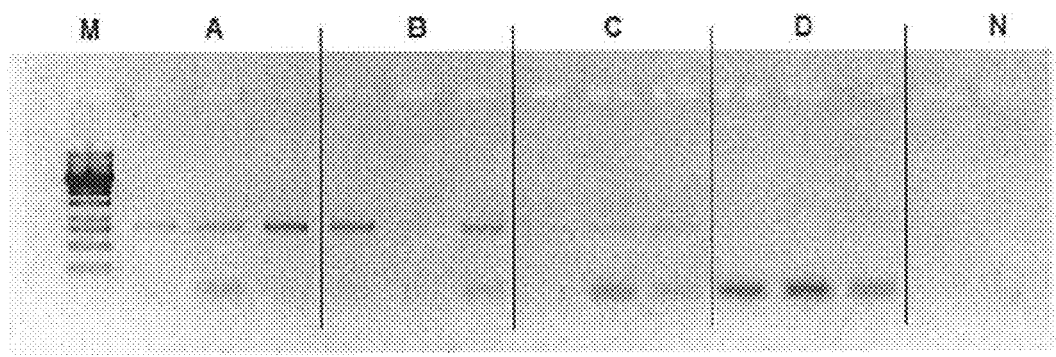

The result is shown in FIG. 32: M: marker, DNA ladder; A: sample transfer tool coated with 0.5% aqueous solution of A-Carrageenan; B: sample transfer tool coated with 0.1% aqueous solution of A-Carrageenan; C: sample transfer tool coated with 0.05% aqueous solution of A-Carrageenan; D: untreated sample transfer tool; N: negative control (no template control)

Conclusion:

The transfer of an EDTA-treated rabbit blood sample into a 10 μl PCR using a plastic toothpick coated with a 0.5% aqueous A-carrageenan solution enables the subsequent amplification of a 813 bp sized DNA fragment, whereas the use of an untreated toothpick does not result in the amplification of the target fragment.

Example 33: Dextran Sulfate 0.01%-1.5% with Tobacco

Sample material: Tobacco leave, stored in the refrigerator for two weeks

Description of tool (kind and amount of active substances and auxiliary agents): Plastic toothpick treated with 38 IU heparin/ml in 10% Tween®20 solution or with dextran sulfate concentrations of 0.01%-1.5% in 10% Tween®20 solution.

Primer: Primer pair #10

PCR program: #1

Figure 33:
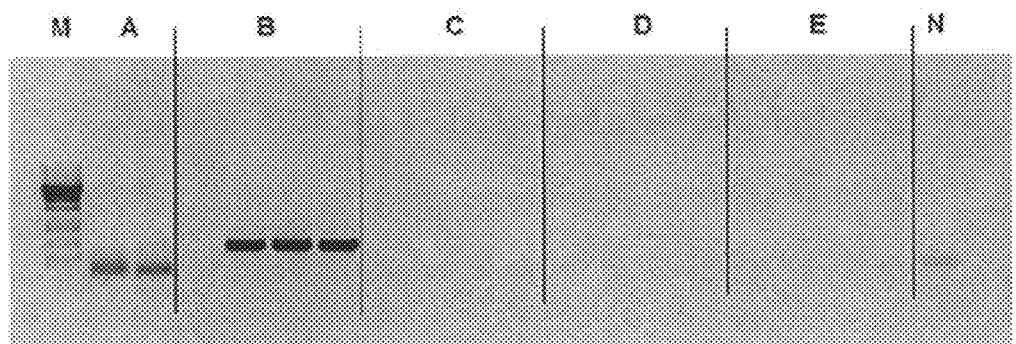
Figure 33:
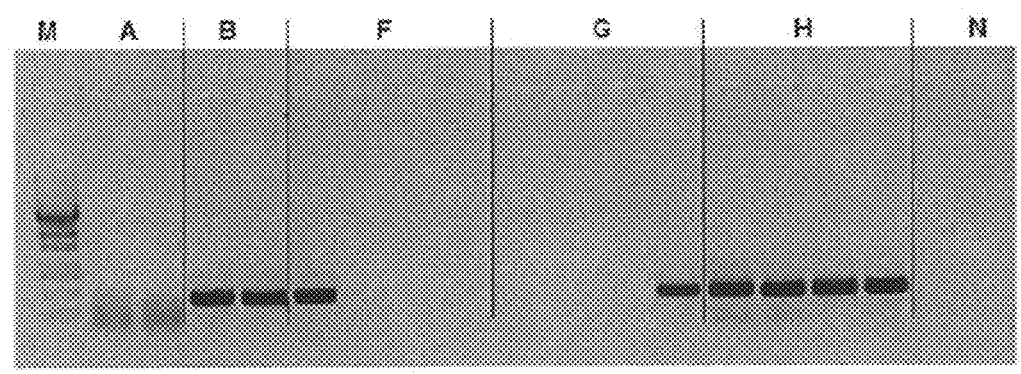

The result is shown in FIG. 33: M: marker, DNA ladder; A: untreated toothpicks; B: heparin-treated toothpicks; C: 0.5% dextran sulfate solution for toothpick treatment; D: 1% dextran sulfate solution for toothpick treatment; E: 1.5% dextran sulfate solution for toothpick treatment; F: 0.1% dextran sulfate solution for toothpick treatment; G: 0.05% dextran sulfate solution for toothpick treatment; H: 0.01% dextran sulfate solution for toothpick treatment; N: negative control (no template control)

Conclusion:

A functional inhibitor-inactivating sample transfer tool that can be successfully used for the sample transfer/amplification of tobacco leaves can be prepared by coating toothpicks with a 0.01% dextran sulfate solution.

Example 34: Arabidopsis: Heparin, Dextran Vs. Uncoated and NK

Sample material: Leaves from Arabidopsis

Description of tool (kind and amount of active substances and auxiliary agents): Plastic toothpick treated with 38 IU heparin/ml of 10% Tween®20 solution or with dextran sulfate concentrations of 0.01% Tween®20 solution.

Primer: Primer pair #11

PCR program: #1, but with 52° C. annealing temperature

Figure 34:
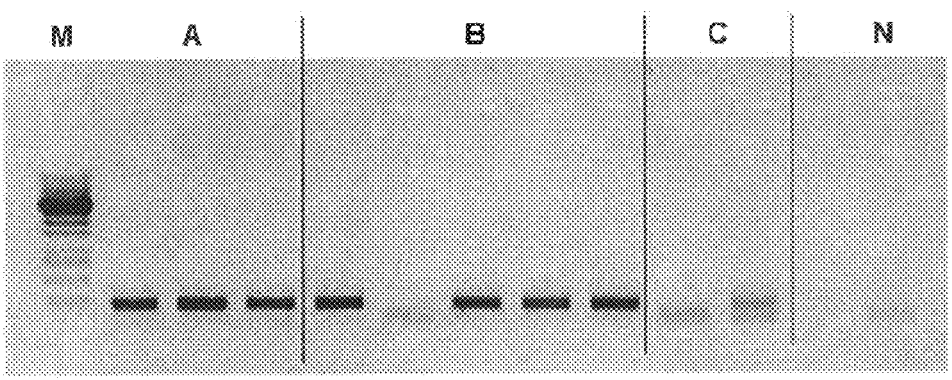

The result is shown in FIG. 34: M: marker, DNA ladder; A: heparin-coated toothpicks; B: toothpicks coated with dextran sulfate (0.01%); C: uncoated toothpicks; N: negative control (no template control)

Conclusion:

Sample transfer tools coated with dextran sulfate can be successfully used for sample transfer not only for tobacco leaves, but also for Arabidopsis leaves.

Example 35: Maize: Dextran 0.00%, 0.005%, 0.01% Vs. Uncoated

Sample material: Leaf material from maize

Description of tool (kind and amount of active substances and auxiliary agents): Plastic toothpick treated with dextran sulfate sodium salt in 10% Tween®20

Solution

Primer: Primer pair #8

PCR program: #4

Figure 35:
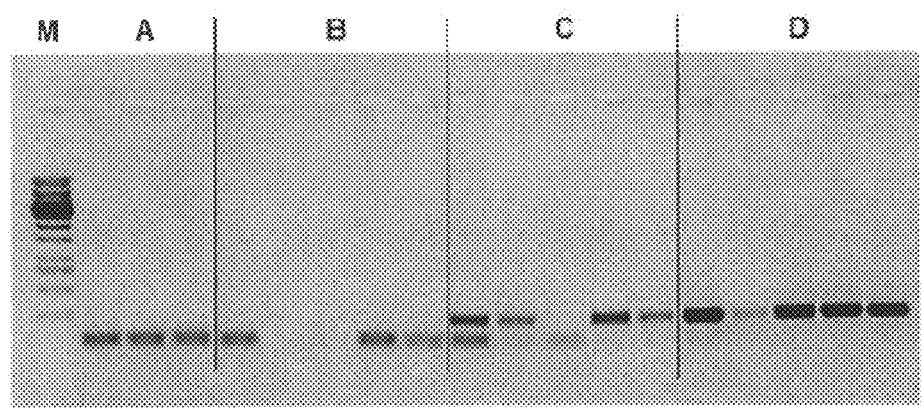

The result is shown in FIG. 35: M: marker—DNA ladder; A: uncoated toothpick for sample transfer; B: toothpick coated with 0.001% dextran sulfate sodium salt in 10% Tween®20; C: toothpick coated with 0.005% dextran sulfate sodium salt in 10% Tween®20; D: toothpick coated with 0.01% dextran sulfate sodium salt in 10% Tween®20

Conclusion:

When uncoated toothpicks are used for the transfer of maize leaf material into PCR, only unspecific by-products are amplified. When toothpicks coated with 0.005% or 0.01% dextran sulfate are used, the target product of 226 bp is formed in the PCR.

Example 36: GITC and GuHCl+/−Tween® with Vine Leaf

Sample material: Vine leaves

Description of tool (kind and amount of active substances and auxiliary agents): Plastic toothpick treated with different chaotropic salts Primer: Primer pair #12

PCR program: #12

Figure 36:
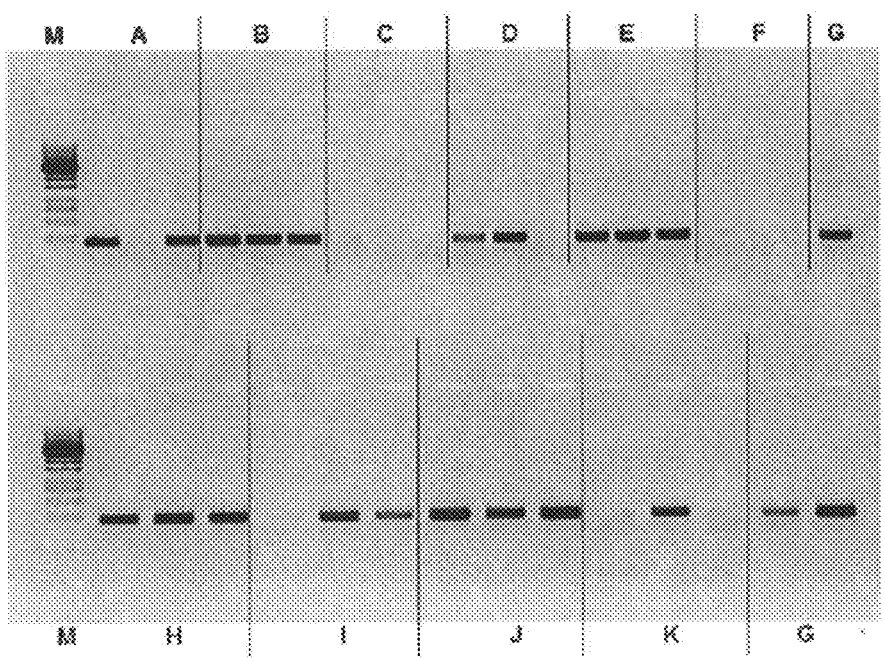

The result is shown in FIG. 36: M: marker, DNA ladder; A: toothpick coating: 4 M GuSCN in 2% Tween®20; B: toothpick coating: 4 M GuSCN in 10% Tween®20; C: toothpick coating: 5 M GuSCN; D: toothpick coating: 5 M GuSCN in 10% Tween®20; E: toothpick coating: LiHeparin-Tween®; F: negative control: toothpick uncoated; G: toothpick coating: 8 M GuHCl in 10% Tween®20; H: toothpick coating: 6.4 M GuHCl in 20% Tween®20; I: toothpick coating: 6.5 M GuHCl; J: toothpick coating: 6.5 M GuHCl in 10% Tween®20; K: toothpick coating: 8 M GuHCl Conclusion:

Using toothpicks coated with chaotropic salt/Tween®20 mixtures for sample transfer can lead to a comparably good amplification of DNA in PCR as using toothpicks coated with heparin/Tween®20. In contrast, when uncoated toothpicks are used for the sample transfer of vine leaf material, no amplificate is formed (F).

Example 37: Tween® as Auxiliary Agent Replaced by Water or Propylene Glycol with Leaves and Blood Sample material: Vine leaves, rat blood Description of tool (kind and amount of active substances and auxiliary agents): Plastic toothpick treated with heparin-Tween®20, heparin, heparin-polypropylene glycol. (Polypropylene glycol: CAS 25322-69-4, average molecular weight: 2700 g/mol)

Primer: Primer pair #12 (vine leaves), primer pair #3 (rat blood)

PCR program: #12 (vine leaves); #17 (rat blood)

Figure 37:
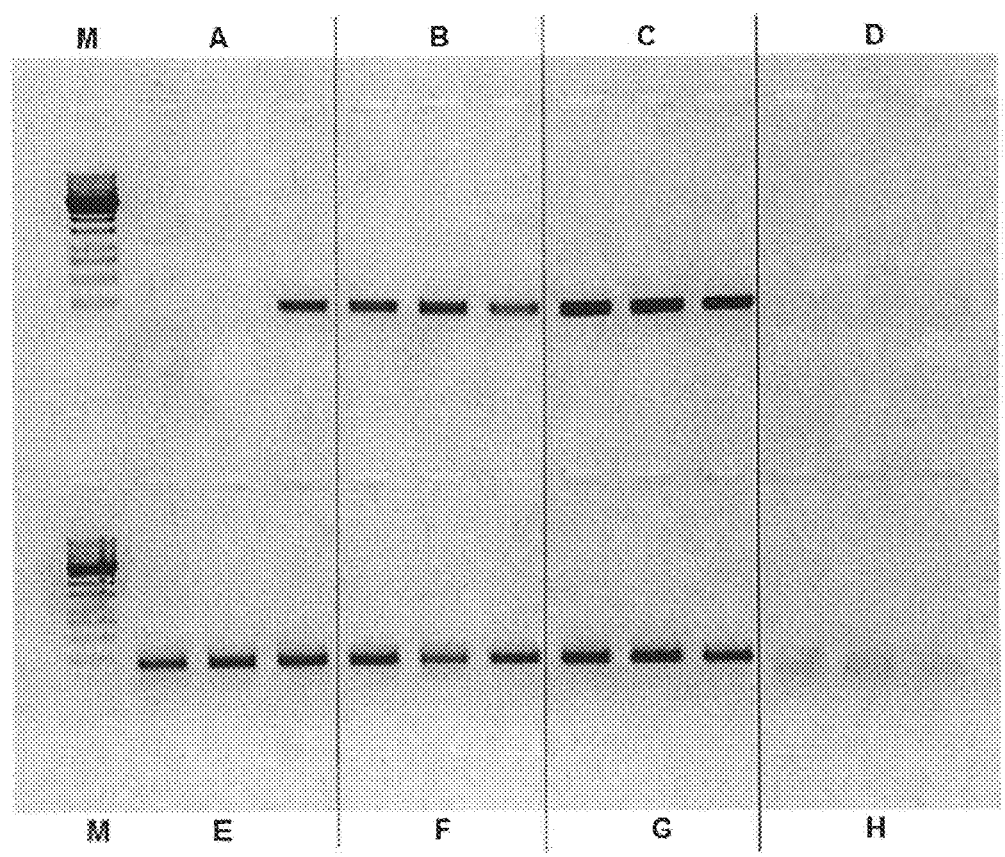

The result is shown in FIG. 37: M: marker—DNA ladder; for the sample transfer for different sample materials, toothpicks were used that had previously been coated with different solutions; A: vine leaf; coating: heparin in water; B: vine leaf; coating: heparin in 10% polypropylene glycol; C: vine leaf; coating: heparin in 10% Tween®20; D: vine leaf; coating: none; E: blood; coating: heparin in water; F: blood; coating: heparin in 10% polypropylene glycol; G: blood; coating: heparin in 10% Tween®20; H: blood; coating: none Conclusion:

The use of a viscous non-drying auxiliary agent for dissolving and coating the active substance heparin onto a toothpick improves its effectiveness. As an alternative to the auxiliary agent Tween®20, polypropylene glycol may also be used as an auxiliary agent.

Example 38: λ-Carrageenan with Blood

Sample material: Rat blood

Description of tool (kind and amount of active substances and auxiliary agents): Plastic toothpick coated with 1% λ-carrageenan (CAS 9064-57-7) in 10% Tween®20 solution Primer: Primer pair #3

PCR program: #17

Figure 38:
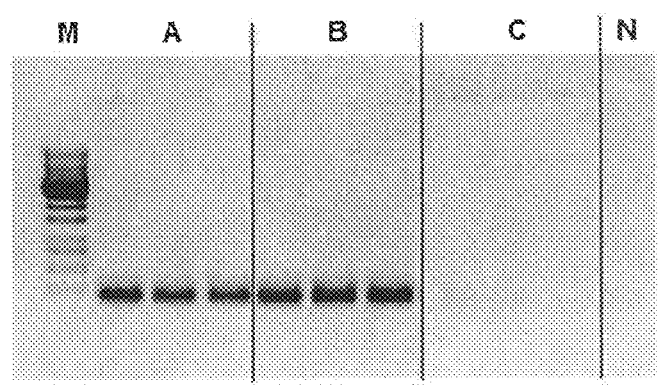

The result is shown in FIG. 38: M: marker—DNA ladder; A: toothpick coated with heparin in 10% Tween®20 solution; B: toothpick coated with a solution of 1% λ-carrageenan, 10% Tween®20; C: uncoated toothpick; D: PCR negative control (no template control)

Conclusion

As an alternative to heparin, λ-carrageenan may also be used as an active substance for coating sample transfer tools, so that an amplificate having the target size (191 bp) is formed when rat blood is transferred into PCR using a carrageenan-coated tool.

Example 39: λ-Carrageenan with Meat (Goat)

Sample material: Goat meat (raw)

Description of tool (kind and amount of active substances and auxiliary agents): Plastic toothpick coated with a solution of 0.5% λ-carrageenan, 10% Tween®20.

Primer: Primer pair #16

PCR program: #18

Figure 39:
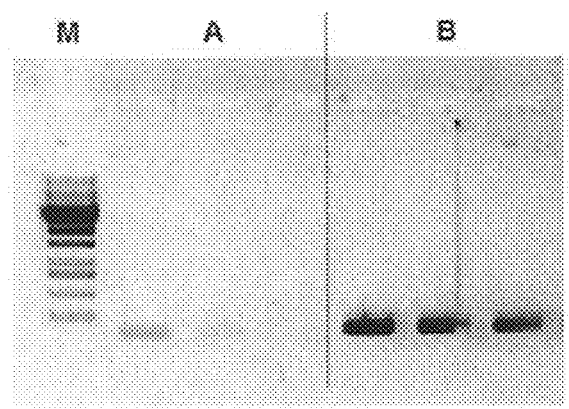

The result is shown in FIG. 39: M: marker, DNA ladder; A: untreated toothpick for sample transfer; B: toothpick was coated with 0.5% λ-carrageenan, 10% Tween®20 before the sample transfer.

Conclusion:

If sample material from goat raw meat is taken up by pricking by means of a toothpick treated with λ-carrageenan/Tween®20 and transferred to the PCR, the target fragment of 142 bp can be amplified, whereas when an untreated toothpick is used, no amplificate, or much less thereof, is formed.

Examples Group V: Different Materials and Shapes of the Sample Transfer Tool

Example 40: Toothpick, Pipette Tips, Paper Clip

Figure 40:
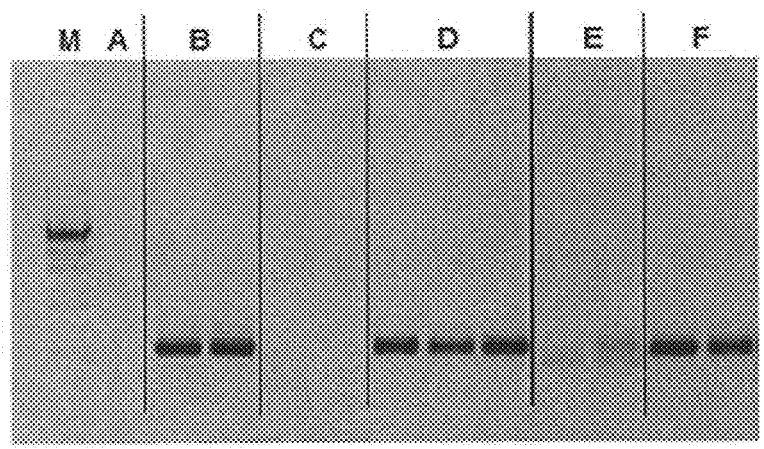

Sample material: Cotton leaves
Description of tool (kind and amount of active substances and auxiliary agents): Plastic toothpick and pipette tip 0.5-10 µl, paper clip treated with 38 IU heparin/ml of 10% Tween®20 solution
Primer: Primer pair #5
PCR program: #1
The result is shown in FIG. 40: M: marker—DNA ladder; A: plastic toothpick uncoated; B: plastic toothpick coated with heparin/Tween; C: pipette tip uncoated; D: pipette tips coated with heparin/Tween; E: wire (paper clip, bent up) uncoated; F: wire (paper clip, bent up) coated with heparin/Tween®
Conclusion:
Not only plastic toothpicks can be converted to inhibitor-inactivating sample transfer tools by coating with an active substance, but hollow tubular pipette tips as well as wire (bent up paper clip) also can.

Example 41: Combitips Interior Part, Paper Clip with Cotton Leaf

Figure 41:
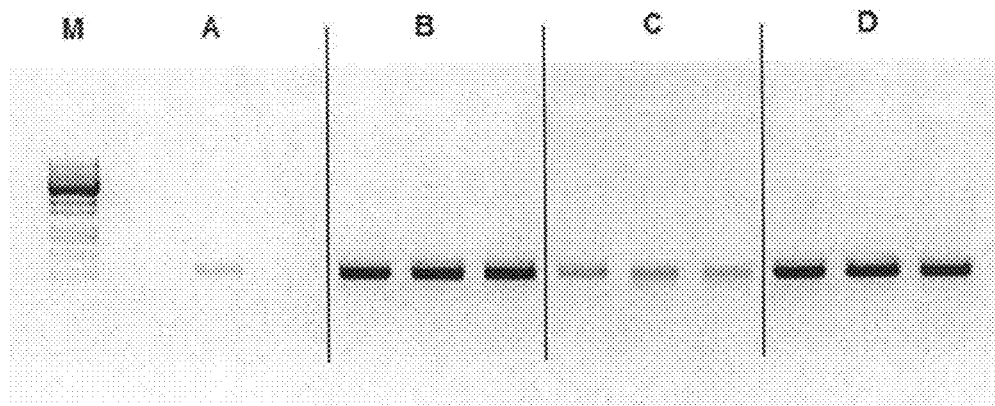

Sample material: Cotton leaves
Description of tool (kind and amount of active substances and auxiliary agents): plastic rods (interior part of a Combitip 100 µl), wire (paper clip) treated with 38 IU heparin/ml of 10% Tween®20 solution
Primer: Primer pair #5
PCR program: #12
The result is shown in FIG. 41: M: marker—DNA ladder; A: interior part of a Combitip uncoated; B: interior part of a Combitip coated; C: wire (paper clip) uncoated; D: wire (paper clip) coated
Conclusion:
An inhibitor-inactivating sample transfer tool can be prepared by coating plastic rods (interior part of a Combitip pipette tip) other than toothpicks and a bent-up paper clip with heparin/Tween®20.

Example 42: Polystyrene Rods from Weighing Boats with Blood

Figure 42:
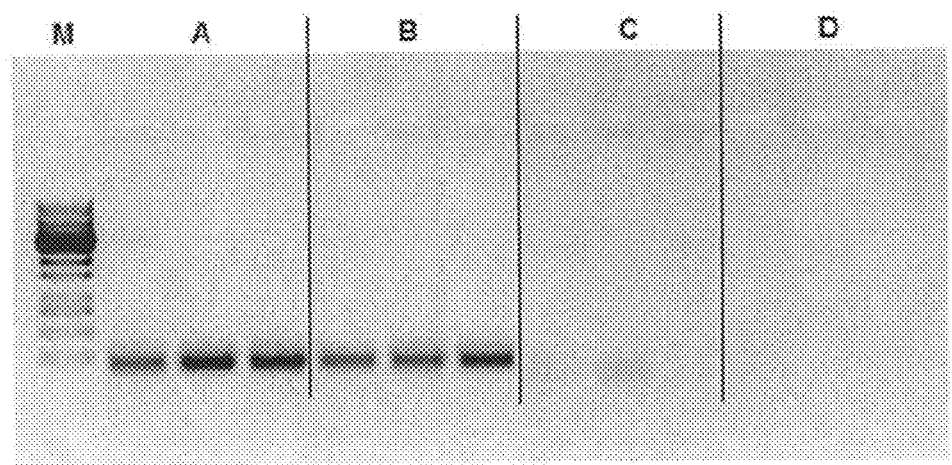

Sample material: Rat blood
Description of tool (kind and amount of active substances and auxiliary agents): Plastic toothpick and a segment (cut to have a sharpened point) of a polystyrene weighing dish treated with 38 IU heparin/ml of 10% Tween®20 solution
Primer: Primer pair #3
PCR program: #17
The result is shown in FIG. 42: M: marker—DNA ladder; A: toothpick coated with heparin/Tween®20; B: segment cut to have a sharpened point of a polystyrene weighing dish coated with heparin/Tween®20; C: toothpick (uncoated); D: segment cut to have a sharpened point of a polystyrene weighing dish (uncoated)
Conclusion:
In addition to plastics that are typically used for toothpicks, sharply tapering rods of polystyrene material may also be used as the tool material for preparing inhibitor-inactivating sample transfer tools.

Example 43: Pipette Tip with Blood

Figure 43:
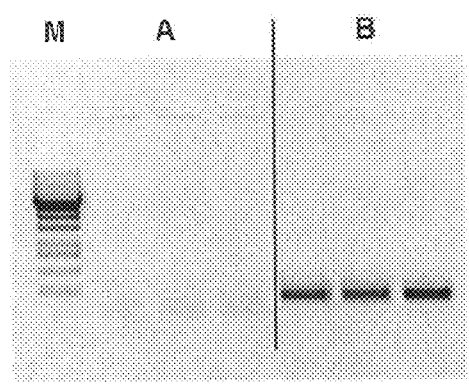

Sample material: Rat blood
Description of tool (kind and amount of active substances and auxiliary agents): Tip of a 10/20 µl pipette as typically used in laboratories (from the company Starlab) coated with 38 IU heparin/ml of 10% Tween®20 solution
Primer: Primer pair #3
PCR program: #17
The result is shown in FIG. 43: M: marker, DNA ladder; A: uncoated pipette tip; B: coated pipette tip
Conclusion:
Tips of pipettes as typically used in laboratories may also be converted to an inhibitor-inactivating sample transfer tool by coating them with heparin/Tween®20.

Example 44: Determination of the Quantities of Active Substance on the Transfer Tool A. Tested concentrations of active substance in the coating solution that were found to be effective.

| Example | Concentration of active substance in the coating solution with positive results |
|---|---|
| 1 | 24 I.U., 240 IE heparin/ml |
| 2 | 240 I.U. heparin/ml |
|   | 40 I.U. heparin/ml |
| 4 | 40 I.U. heparin/ml |
| 5 | 40 I.U. heparin/ml |
| 6 | 38 I.U. heparin/ml |
| 7 | 38 I.U. heparin/ml |
| 8 | 38 I.U. heparin/ml |
| 9 | 38 I.U. heparin/ml |
| 10 | 40 I.U. heparin/ml |
| 11 | 38 I.U. heparin/ml |
| 12 | 38 I.U. heparin/ml |
| 13-28 | 38 I.U. heparin/ml |
| 29 | 1% and 5% chondroitin sulfate sodium salt |
| 30 | 5% chondroitin sulfate sodium salt, 1%, 0.5%, 0.1% dextran sulfate |
| 31 | 6M GITC, 90 mM EDTA, 1.5% Tween ®, 50 mM Tris pH 8 |
| 32 | 0.5%, 0.1%, 0.05% carrageenan |
| 33 | 0.05%, 0.01% dextran sulfate |
| 34 | 0.01% dextran sulfate |
| 35 | 0.01%, 0.005% dextran sulfate |
| 36 | 4M, 5M GITC, 6.4M, 8M GuHCl |
| 37 | heparin |
| 38 | 1% carrageenan |
| 39 | 0.5% carrageenan |
| 40 | 38 I.U. heparin |
| 41 | 38 I.U. heparin |
| 42 | 38 I.U. heparin |
| 43 | 38 I.U. heparin |

Ranges of effective concentrations of the active substance in the coating solutions:
Heparin: 24-240 IU/ml
Chondroitin sulfate sodium salt: 1%-5%
Dextran sulfate: 0.005-1%
Carrageenan: 0.05%-1%
Chaotropic salt: 4 M-8 M B. Amount of liquid taken up by a toothpick by immersing about 1 cm of the tip.

The amount of liquid adhering to the tip of the toothpick after immersion was at first estimated to be 5 nl (based on measurements with ink), but this appeared to be rather small, and therefore, a direct measurement with 200 toothpicks was effected.

Measured amount of coating solution that adheres to the toothpick for 10 mm immersion depth: about 0.132 µl per toothpick (mean of 200 toothpicks).

C. Determination of the surface area of the toothpick tip for an immersion depth of 10 mm.

Diameter at 10 mm level: 1.0-1.4. Average: 1.2 mm

Diameter at 1 mm level: 0.54-0.60 mm. Average: 0.57 mm.

Mean diameter: 0.885 mm

Mean circumference: $2Pi*r=0.885*3.14=2.78$ mm

Cylinder area: $U*h=2.78*10=27.8$ mm$^2$.

Area of tip: $F=Pi*r^2=(0.57/2)^2*3.14=0.255$ mm$^2$

Surface of toothpick for an immersion depth of 10 mm: $27.8+0.895=28.1$ mm$^2$

Measured amount of coating solution that adheres to the toothpick for 10 mm immersion depth: about 0.132 µl per toothpick (average of 200 toothpicks).

D. Calculation of the amount of active substance per mm$^2$ of coated toothpick surface.

Heparin:

24-240 IU/ml→this is 0.003-0.03 IU of heparin per 0.132 µl of adhering coating solution.

Distributed to 28.1 mm$^2$, one obtains: 0.0001-0.001 IU of heparin/mm$^2$ or 0.01-0.1 IU of heparin/cm$^2$.

Conclusion:

The coated surface of the toothpick with heparin as the active substance contains a quantity of heparin of about 0.01-0.1 IU of heparin cm$^2$.

Chondroitin sulfate sodium salt:

1%-5%→1-5 g/100 ml→0.01-0.05 g/ml→10-50 mg/ml→0.01-0.05 mg/µl.

Per 0.132 µl of adhesion solution, this corresponds to 0.0013-0.0066 mg of active substance on the toothpick.

If this amount is distributed over 28.1 mm$^2$, one obtains: 0.000046-0.00023 mg/mm$^2$, or 0.0046-0.023 mg/cm$^2$, or 4.6-23 µl/cm$^2$.

Dextran sulfate:

0.005%-1%→0.005-1 g/100 ml→0.00005-0.01 g/ml or mg/µL→0.05-10 µg/µl

Per 0.132 µl of adhesion solution, this corresponds to 0.0066-1.3 µg of active substance on the toothpick.

If this amount is distributed over 28.1 mm$^2$, one obtains: 0.00023-0.046 µg/mm$^2$, or 0.023-4.6 µg/cm$^2$.

Carrageenan:

0.05%-1% in the solution of active substance, or 0.23-4.6 µg/cm$^2$.

Chaotropic Salt:

4 M-8 M→4-8 mol/l or µmol/µl

Per 0.132 µl of adhesion solution, this corresponds to 0.53-1.1 µmol of active substance on the toothpick.

If this amount is distributed over 28.7 mm$^2$, one obtains: 0.018-0.037 µmol/mm$^2$, or 1.8-3.7 µmol/cm$^2$.

E. Conclusion.

Heparin: 0.01-0.1 IU per cm$^2$ of rod surface

Other polysaccharides: 0.023-23 µg/cm$^2$. Rounded to 0.02-25 µg/cm$^2$

Chaotropic salt: 1.8-3.7 µmol/cm$^2$. Rounded to 1.5-4 µmol/cm$^2$.

---

The invention claimed is:

1. A rod-shaped or tubular sample transfer tool for direct transfer of sample, said sample transfer tool being sized to be suitable for transfer of sample volumes smaller than 1 µl or sample quantities from 10 to 200 µg, and having at least one region designed for contact with a sample containing nucleic acids and coated with one or more active substances, said one or more active substances having an effect on the sample containing nucleic acids, so that materials contained in the sample that would inhibit an enzymatic reaction taking place after the transfer are bound at least in part, or inactivated.

2. The sample transfer tool according to claim 1, wherein
   (i) said enzymatic reaction is a detection reaction selected from PCR, reverse transcription, isothermal amplification, restriction digestion, and sequencing and nucleic acid amplification; and/or
   (ii) said one or more active substances inactivate compounds that inhibit the enzymatic reaction performed after the transfer, or reduce their inhibiting effect, wherein said sample transfer tool is suitable for either binding said compounds/inhibitors by the one or more active substances, or releasing the one or more active substances to thereby inactivate the inhibitors, and wherein said one or more active substances are selected from anticoagulants and polysaccharides; and/or
   (iii) said one or more active substances are released into or dissolved in the sample upon contact with the sample.

3. The sample transfer tool according to claim 1, wherein said one or more active substances are present on said sample transfer tool in a sufficient inhibitor-inhibiting amount.

4. The sample transfer tool according to claim 1, which
   (i) has the shape of a rod, a pin, a needle, a tube or a pipette tip; and/or
   (ii) is made of a solid material selected from plastic, wood, cardboard, paper, ceramics, glass, ceramics, clay, magnesia, metal, and combinations thereof, and/or
   (iii) comprises a region at which the sample transfer tool is held by the operator; and/or
   (iv) is sized to be suitable for transfer of sample volumes from 10 to 500 nl; and/or
   (v) is coated with said active substance(s) in such a way that a sufficient inhibitor-inhibiting amount of said active substance(s) is present on the sample transfer tool; and/or
   (vi) the sample transfer tool is coated with other neutral surfactants and with salts in addition to said one or more active substances.

5. The sample transfer tool according to claim 1, which consists of a plastic rod, toothpick or plastic toothpick coated with heparin.

6. A process for preparing the rod-shaped or tubular sample transfer tool according to claim 1, comprising treating or coating a starting sample transfer tool with said one or more active substances.

7. The process according to claim 6, comprising
   (i) immersing the starting sample transfer tool once or several times into an aqueous solution comprising said one or more active substances, followed by drying the sample transfer tool; or
   (ii) covalently binding said one or more active substances to said starting sample transfer tool.

8. The process according to claim 6, wherein said one or more active substances are selected from anticoagulants and polysaccharides.

9. A method comprising transferring samples containing nucleic acids into an enzymatic reaction with the rod-shaped or tubular sample transfer tool according to claim 1.

10. The method according to claim 9, wherein
    (i) said enzymatic reaction is an enzymatic detection reaction; and/or
    (ii) said samples are selected from body components and body fluids, plants and plant components.

11. A detection method, comprising:
    (a) contacting the rod-shaped or tubular sample transfer tool according to claim 1 with a solid or liquid phase of a sample containing nucleic acids, so that a sufficient amount of said sample containing nucleic acids becomes adhered to said sample transfer tool;
    (b) directly transferring the sample transfer tool to a reaction mixture for an enzymatic detection reaction, and immersing the sample transfer tool into the reaction mixture, so that an amount of said sample containing nucleic acids sufficient for the detection reaction is carried from the sample transfer tool into the enzymatic detection reaction;
    (c) removing the sample transfer tool from the reaction mixture for said enzymatic detection reaction; and
    (d) performing said enzymatic detection reaction.

12. The detection method according to claim 11, wherein
    (i) said sample transfer tool has an influence on the sample containing nucleic acids such that substances contained in the sample that inhibit the enzymatic detection reaction are at least partially inactivated or bound; and/or
    (ii) the enzymatic detection reaction is selected from PCR, reverse transcription, isothermal amplification, restriction digestion, and sequencing and nucleic acid amplification; and/or
    (iii) the samples are selected from body components and body fluids, plants and plant components; and/or
    (iv) said reaction mixture is present in a reaction vessel, in a well of a titration plate, or on a planar plate.

13. The detection method according to claim 11, wherein
    (i) steps (a) and (b) are performed independently of one another, manually by an operator, or by a machine; and/or
    (ii) a sample volume is transferred in steps (a) and (b); and/or
    (iii) the reaction volume of the detection reaction is from 1 to 100 µl; and/or
    (iv) lysis of the sample material is performed before said contacting of step (a).

14. A kit for performing a detection process, comprising one or more of the sample transfer tools according to claim 1.

15. The kit according to claim 14, further comprising reagents, reaction mixtures and/or solvents for the detection reaction, and/or reagents for lysis of a sample material.

16. The sample transfer tool according to claim 2, wherein said one or more active substances are selected from heparin, chondroitin sulfate, heparan sulfate, keratan sulfate, amidopectins, hyaluronic acid, pectins, xanthan, chitosan, oligo-glucosamine, dextran sulfate, carrageenan, methylcellulose, guaran, and chaotropic salts.

17. The sample transfer tool according to claim 3, wherein the one or more active substances is heparin and the heparin is present on the sample transfer tool in a coating of 0.001 to 0.5 $IU/cm^2$; or the one or more active substances is a polysaccharide other than heparin and the polysaccharide other than heparin is present on the sample transfer tool in a coating of 0.005 to 50 $\mu g/cm^2$; or the one or more active substances is a chaotropic salt and the chaotropic salt is present on the sample transfer tool in a coating of 0.1 to 50 $\mu mol/cm^2$.

18. The sample transfer tool according to claim 4, which is sized to be suitable for transfer of sample volumes from 50 to 200 nl; or sample quantities from 50 to 200 μg.

19. The method according to claim 10, wherein the enzymatic detection reaction is selected from the group consisting of PCR, reverse transcription, isothermal amplification, restriction digestion, and sequencing and nucleic acid amplification; and/or said samples are selected from blood, urine, saliva, cells, tissues, stool, and plant material.

20. The detection method according to claim 12, wherein the samples are selected from blood, urine, saliva, cells, tissues, stool, and plant material.

\* \* \* \* \*